United States Patent
Hynes et al.

(10) Patent No.: US 12,161,560 B2
(45) Date of Patent: Dec. 10, 2024

(54) INTEGRAL GRAFT INTERBODY DEVICES

(71) Applicant: Warsaw Orthopedic, Inc., Warsaw, IN (US)

(72) Inventors: Richard A. Hynes, Melbourne Beach, FL (US); Jonathan M. Dewey, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/392,679

(22) Filed: Aug. 3, 2021

(65) Prior Publication Data
US 2023/0043823 A1 Feb. 9, 2023

(51) Int. Cl.
*A61F 2/44* (2006.01)
*A61F 2/30* (2006.01)

(52) U.S. Cl.
CPC ........ *A61F 2/4455* (2013.01); *A61F 2/30771* (2013.01); *A61F 2002/30784* (2013.01)

(58) Field of Classification Search
CPC .............. A61F 2/44–447; A61F 2/4611; A61F 2002/30818–30831
See application file for complete search history.

(56) References Cited

U.S. PATENT DOCUMENTS

| | | | |
|---|---|---|---|
| 4,955,908 A * | 9/1990 | Frey | A61F 2/442 623/17.16 |
| 6,176,882 B1 | 1/2001 | Biedermann et al. | |
| 6,245,108 B1 | 6/2001 | Biscup | |
| 6,863,689 B2 * | 3/2005 | Ralph | A61B 17/025 623/17.11 |
| 7,118,579 B2 | 10/2006 | Michelson | |
| 7,575,599 B2 | 8/2009 | Villiers et al. | |
| 7,655,043 B2 | 2/2010 | Peterman et al. | |
| 7,758,644 B2 | 7/2010 | Trieu | |
| 7,875,078 B2 | 1/2011 | Wysocki et al. | |
| 7,988,733 B2 * | 8/2011 | Shimp | A61F 2/4455 623/17.11 |
| 8,211,177 B2 | 7/2012 | Richelsoph | |
| 8,398,713 B2 | 3/2013 | Weiman | |
| 8,535,380 B2 | 9/2013 | Greenhalgh et al. | |

(Continued)

FOREIGN PATENT DOCUMENTS

EP 1838248 3/2013

OTHER PUBLICATIONS

Frisch, Richard F., et al., "Clinical and radiograph analysis of expandable versus static lateral lumbar interbody fusion devices with two-year follow-up," Journal of Spine Surgery 2018;4(1), Mar. 1, 2018, pp. 62-71.

*Primary Examiner* — Eduardo C Robert
*Assistant Examiner* — Steven J Cotroneo
(74) *Attorney, Agent, or Firm* — Fletcher Yoder, P.C.

(57) ABSTRACT

An interbody spinal implant including a body portion having a superior side, an inferior side and a lateral side connecting the superior side and the inferior side, at least one of the superior side or the inferior side comprises a bone contacting surface operable to be coupled to an anatomical structure of a patient; and a plurality of uniform features formed in the bone contacting surface, wherein each uniform feature of the plurality of uniform features comprise a planar peak or a round peak and are dimensioned to increase a surface area of the bone contacting surface to promote bone growth.

14 Claims, 21 Drawing Sheets

(56) References Cited

U.S. PATENT DOCUMENTS

| | | |
|---|---|---|
| 8,574,300 B2 | 11/2013 | McManus et al. |
| 8,864,829 B1 * | 10/2014 | Bruffey ............. A61F 2/442 |
| | | 623/17.11 |
| 8,936,641 B2 | 1/2015 | Cain |
| 8,940,049 B1 | 1/2015 | Jimenez et al. |
| 8,979,934 B2 * | 3/2015 | Kirschman ......... A61F 2/3094 |
| | | 623/17.11 |
| 9,078,767 B1 | 7/2015 | McLean |
| 9,101,489 B2 | 8/2015 | Protopsaltis et al. |
| 9,408,708 B2 | 8/2016 | Greenhalgh |
| 9,408,710 B2 | 8/2016 | Purcell et al. |
| 9,526,627 B2 | 12/2016 | Tabor et al. |
| 9,539,108 B2 | 1/2017 | Glerum et al. |
| 9,622,876 B1 | 4/2017 | Greenhalgh et al. |
| 9,622,878 B2 | 4/2017 | Grotz |
| 9,901,459 B2 | 2/2018 | Faulhaber |
| 9,974,662 B2 | 5/2018 | Hessler et al. |
| 10,478,313 B1 * | 11/2019 | Sweeney, III ......... A61F 2/4611 |
| 10,507,116 B2 | 12/2019 | Shoshtaev |
| 10,806,596 B2 | 10/2020 | Iott et al. |
| 10,888,433 B2 | 1/2021 | Frasier et al. |
| 11,129,728 B1 * | 9/2021 | Molina ............. A61F 2/447 |
| 2002/0049497 A1 * | 4/2002 | Mason ............. A61F 2/447 |
| | | 623/17.11 |
| 2005/0027360 A1 * | 2/2005 | Webb ............. A61B 17/1671 |
| | | 623/17.11 |
| 2013/0023990 A1 * | 1/2013 | Zipnick ............ A61F 2/442 |
| | | 623/17.16 |
| 2013/0110248 A1 * | 5/2013 | Zipnick ............ A61F 2/442 |
| | | 623/17.16 |
| 2018/0243097 A1 * | 8/2018 | Jones ............. B33Y 50/00 |
| 2019/0053910 A1 * | 2/2019 | Sansur ............ A61F 2/30771 |
| 2019/0091027 A1 * | 3/2019 | Asaad ............. A61F 2/447 |
| 2019/0269521 A1 | 9/2019 | Shoshtaev |
| 2019/0328539 A1 * | 10/2019 | Suh ............... A61F 2/442 |
| 2020/0360155 A1 * | 11/2020 | Abdou ............. A61B 17/8695 |
| 2022/0031469 A1 * | 2/2022 | Suh ............... A61F 2/447 |

\* cited by examiner

INTEGRAL GRAFT INTERBODY DEVICES

FIELD

The present technology is related generally to interbody devices having raised surface feature and graft features integrated therein. Other aspects are also described and claimed.

BACKGROUND

The spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the vertebrae and discs may become diseased or infected, develop deformities such as tears and cracks, or simply lose structural integrity, for example bulge or flatten. These impaired vertebrae and discs can result in a lack of proper biomechanical support, and are often associated with chronic back pain.

Several surgical techniques have been developed to address spinal defects, such as vertebral or disc degeneration, deformity, or both. Spinal fusion has become a recognized surgical procedure for mitigating back and neck pain by restoring biomechanical and anatomical integrity to the spine. Spinal fusion techniques may involve the removal, or partial removal, of at least one intervertebral disc and preparation of the disc space for receiving an implant by shaping the exposed vertebral endplates. Such techniques may also involve removing all or part of the vertebral body located proximate the disc. An interbody device is then inserted.

An interbody device such as a spinal implant may be inserted during a spinal fixation procedure using an anterior, lateral, posterior, or transverse spinal approach. A discectomy may be performed to remove or partially remove a defective or damaged intervertebral disc. The discectomy may create a space for one or more spinal implants. The amount of removed disc material may correspond to the size and type of the spinal implant or spinal implants to be inserted. A corpectomy is a surgical procedure that involves removing all or part of the vertebral body (in Latin called a "corpus vertebrae," hence the name corpectomy), usually as a way to decompress the spinal cord and nerves. A corpectomy is often performed in association with some form of discectomy.

Several interbody implant systems have been introduced to facilitate interbody fusion. One such system includes a cage implant which is generally shaped to mimic the anatomical contour of the vertebral body. Another system may include an adjustable cage or implant system that allows the caretaker to adjust the height of the implant. Such height adjustment provides an ability to intra-operatively tailor the implant height to match the natural spacing between the vertebrae. In turn, this ability to tailor the implant height reduces the number of sizes that must be kept on hand to match the variable anatomy of the patients.

SUMMARY

An aspect of the disclosure is directed to an interbody device having structures or features for maximizing surface area contact for bone to grow onto or into the implant and a graft material integrated within the implant. The interbody device could be an expandable or static interbody device such as an implant or cage used to replace a damaged spinal disk during a spinal fusion procedure. In some aspects, the interbody device may be a unibody device and/or include endplates having the surface maximizing structures or features and graft material to promote bone growth on and/or into the device. For example, the unibody device and/or endplates could have holes or channel like structures built in that hold preformed graft material, or the graft material may be integrated into the device using an additive process. In other aspects, the surface and/or graft features could be any sort of structure that will increase the total surface area of the device that is in contact with the bone and/or promote or enhance bone growth on or into the device.

In one aspect, the present disclosure includes an interbody spinal implant including a body portion having a superior side, an inferior side and a lateral side connecting the superior side and the inferior side, at least one of the superior side or the inferior side includes a bone contacting surface operable to be coupled to an anatomical structure of a patient; and a plurality of uniform features formed in the bone contacting surface, wherein each uniform feature of the plurality of uniform features includes a planar peak or a round peak and are dimensioned to increase a surface area of the bone contacting surface to promote bone growth. In some aspects, each uniform feature includes a continuous length dimension extending from an anterior side to a posterior side of the body portion. In some aspects, the plurality of uniform features are arranged in a linear pattern and each of the uniform features are discrete protrusions arranged to form the linear pattern. In another aspect, each uniform feature includes an undercut, and the undercut of adjacent features forms a trough between each of the uniform features. In some aspects, the superior side includes the bone contacting surface and the inferior side includes a bone contacting surface, and the plurality of uniform features extend from the bone contacting surface of the superior side to the bone contacting surface of the inferior side. In some aspects, each uniform feature is separated by a channel extending from an anterior side to a posterior side of the body, and wherein a width dimension of the channel at the anterior side is different than a width dimension at the posterior side. In some aspects, the implant further includes a mesh coupled to the plurality of uniform features to further increase a surface area of the bone contacting surface to promote bone growth. In other aspects, a surface coating is applied to the plurality of uniform features. In still further aspects, a plurality of holes may be formed through the bone contacting surface of the superior side or the inferior side and a graft material embedded within the plurality of holes. In some aspects, the body portion is a unibody cage.

In another aspect, the disclosure is directed to an interbody spinal implant including a cage having a superior side connected to an inferior side, at least one of the superior side or the inferior side includes a bone contacting surface operable to be coupled to an anatomical structure of a patient; a plurality of raised features formed in the bone contacting surface, the plurality of raised features are dimensioned to increase a surface area of the bone contacting surface; and a plurality of graft features embedded in the bone contacting surface, wherein the plurality of graft features include at least one graft feature positioned between each raised feature of the plurality of raised features that promotes bone growth through the bone contacting surface. In some aspects, the least one graft feature includes a discrete unit of graft material positioned within a hole formed through the bone contacting surface. In some aspects, the plurality of raised features and the plurality of graft features are arranged in an alternating linear pattern. In some aspects, the at least one graft feature comprises a length dimension that runs parallel to a length dimension of the plurality of raised features. In still further aspects, the plurality of graft features may be embedded in the plurality of raised features. In some aspects, the cage includes a first endplate forming the superior side and a second endplate forming the inferior side. The cage may be an expandable cage.

In still further aspects, the disclosure is directed to a method of manufacturing an interbody spinal implant including providing a body portion having a superior side, an inferior side, a lateral side connecting the superior side and the inferior side, and a plurality of holes formed in the superior side or the inferior side; processing the body portion to fill the plurality of holes with a graft material operable to promote bone growth; and processing the body portion to form a plurality of raised features on the superior side or the inferior side that increase a bone contacting surface area of the body portion. In some aspects, processing the body portion to fill the plurality of holes includes inserting discrete units of the graft material into the plurality of holes. In some aspects, processing the body portion to fill the plurality of holes includes depositing layers of the graft material to the body portion until the plurality of holes are filled by the graft material.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect in this disclosure are not necessarily to the same aspect, and they mean at least one.

DETAILED DESCRIPTION

In this section we shall explain several preferred aspects of the disclosure with reference to the appended drawings. Whenever the shapes, relative positions and other aspects of the parts described in the aspects are not clearly defined, the scope of the invention is not limited only to the parts shown, which are meant merely for the purpose of illustration. Also, while numerous details are set forth, it is understood that some aspects of the invention may be practiced without these details. In other instances, well-known structures and techniques have not been shown in detail so as not to obscure the understanding of this description.

The terminology used herein is for the purpose of describing particular aspects only and is not intended to be limiting of the disclosure. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Figure 1:
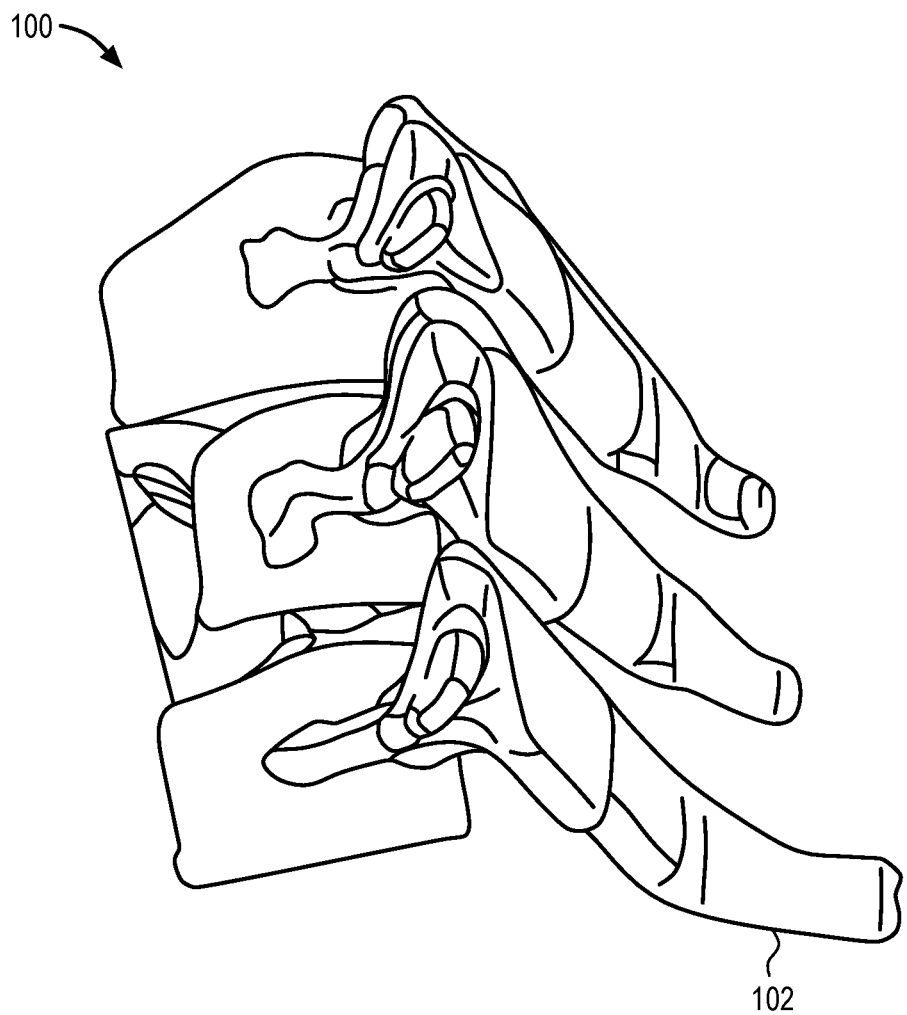
FIG. 1 shows a representation of a functional spinal unit.
Figure 2A:
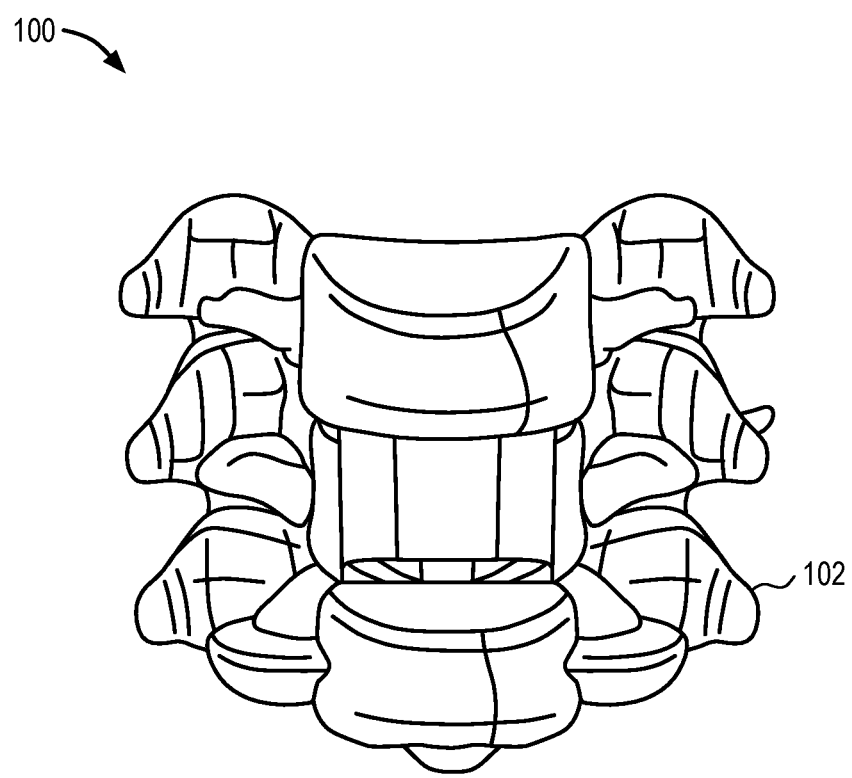
FIG. 2A shows an anterior view of a partial corpectomy of a vertebra.
Figure 2B:
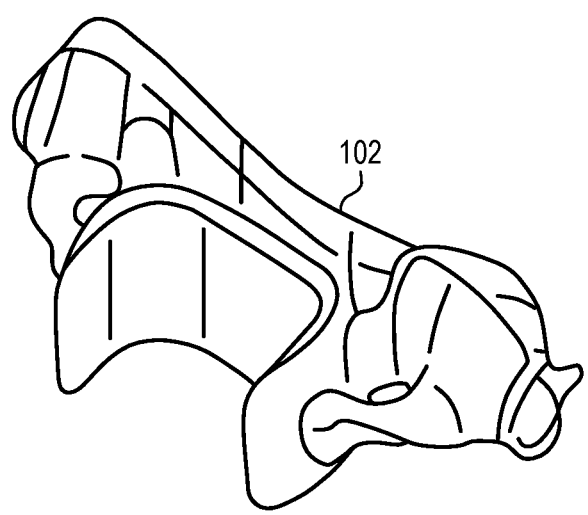
FIG. 2B shows a perspective view of a partial corpectomy of a vertebra with a portion of the vertebral endplate removed.
Figure 2C:
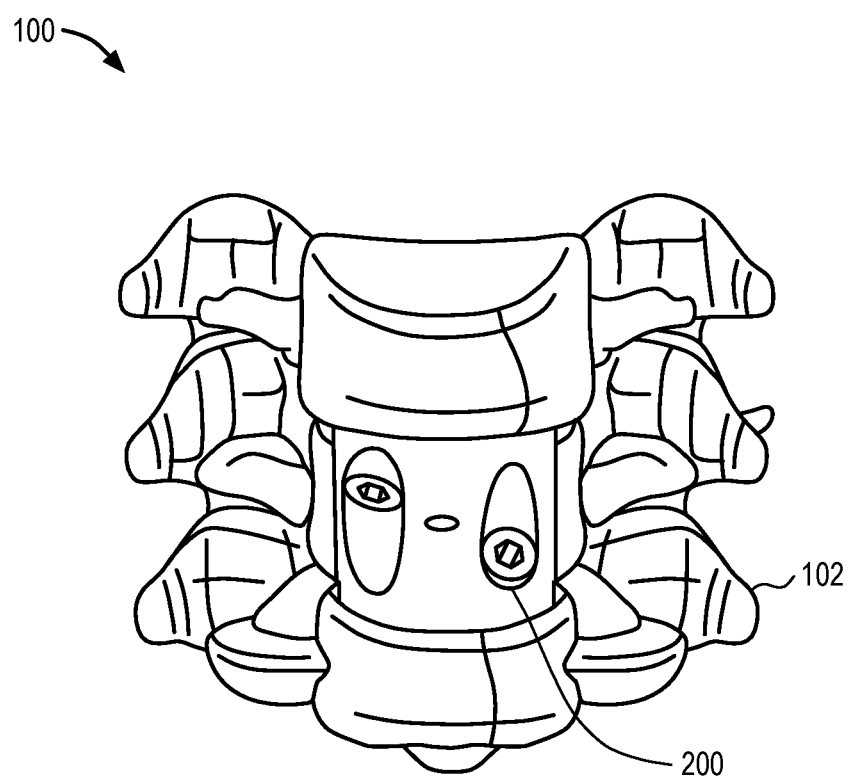
FIG. 2C shows an implant inserted into the channel of the vertebra.

Referring now to FIG. 1, in which like reference numbers refer to like elements throughout the various figures that comprise the drawing, implants in accordance with certain aspects of the disclosure stand in the place of at least a portion of at least one vertebrae 102, including in the place of a functional spinal unit 100 which is illustrated in FIG. 1. The implants are preferably used in accordance with surgical procedures, as illustrated in FIG. 2A and FIG. 2B, that retain some portion of a vertebrae 102. FIG. 2A shows an anterior view of a partial corpectomy of a vertebra 102, and FIG. 2B shows a perspective view of a partial corpectomy of a vertebra 102 with a portion of the vertebral endplate removed. Such surgical procedures allow the implant to be seated in place of the removed portion and contact the extant bone, while the top and bottom surfaces of the implant contact the inferior and superior surfaces of adjacent vertebrae 102, including vertebral endplate bone. FIG. 2C shows an implant 200 inserted into the channel of the vertebra 102.

Implants in accordance with certain aspects of the disclosure may be made of a durable material such as metals, but can also be made of other durable materials such as, but not limited to, plastic, polymeric, silicone, ceramic, bone, and composites of any such materials. Suitable polymers include polyether ether ketone (PEEK) and ultra-high molecular weight polyethylene (UHMWPE), as well as urethane dimethacrylate (DUDMA)/tri-ethylene glycol dimethacrylate (TEDGMA) blended resin. Certain aspects of the disclosure may be comprised of a biocompatible, polymeric matrix reinforced with bioactive fillers, fibers, or both. Certain aspects of the disclosure may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also include any number of pure metals, metal alloys, or both. Titanium and its alloys are generally preferred for certain embodiments of the invention due to their acceptable, and desirable, strength and biocompatibility. Suitable metals may include titanium, an alloy of titanium such as an aluminum and vanadium alloy of titanium (e.g., 6-4), a nickel alloy of titanium such as nitinol, a cobalt chromium alloy, surgical grade steel, stainless steel, or stainless steel alloy. In this manner, certain aspects of the interbody spinal implant disclosed herein may have improved structural integrity and may better resist fracture during implantation by impact. Interbody spinal implants, as now taught, may therefore be used as a distractor or trial implant during implantation.

The disclosure relates to an implant having surface features and/or graft materials embedded into the implant during manufacture to enhance bone growth on or in the implant once implanted in a patient. Certain aspects of the disclosure may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. The ability to achieve spinal fusion is directly related to the available vascular contact area over which fusion is desired, the quality and quantity of the fusion mass, and the stability of the interbody spinal implant. The interbody spinal implants disclosed herein include surface features and/or embedded graft features or material that may improve and/or increase the vital surface area over which fusion may occur and may better bear the considerable biomechanical loads presented through the spinal column. Interbody spinal implants as disclosed herein may also facilitate osteointegration with the surrounding living bone.

Figure 3:
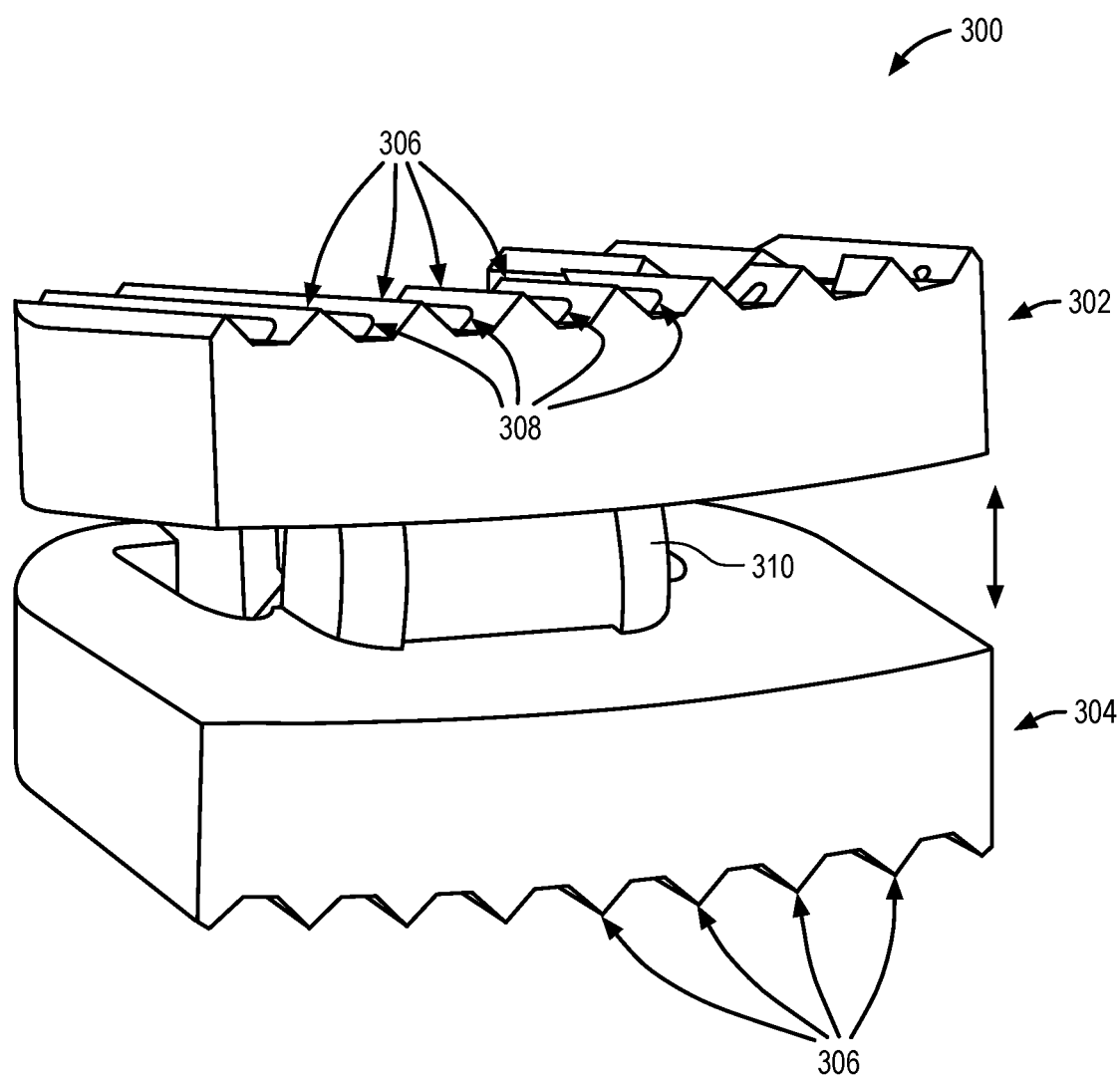
FIG. 3 shows a perspective view of one aspect of an interbody spinal implant.

In one aspect, the implant may be an expandable interbody device as shown in FIG. 3. Representatively, in one aspect, implant 300 may be an expandable or adjustable corpectomy cage. In this aspect, implant 300 may include a first (top) endplate 302 connected to a second (bottom) endplate 304 by a connector 310. In some aspects, the connector 310 may be considered a body, a column, a lateral side, or any other structure suitable for connecting first endplate 302 to second endplate 304. The first (top) endplate 302 and the second (bottom) endplate 304 may move towards or away from each other in the direction of the arrow to expand, contract, or otherwise adjust the implant.

In some aspects, the first (top) endplate 302 may be considered or referred to herein as a superior side of the implant because it faces toward the head end of the body when inserted in the body/coronally. The second (bottom) endplate 304 may be considered or referred to herein as an inferior side of the implant because it faces away from the head when inserted in the body. In this aspect, when implant 300 is inserted in the body, the top or superior surface of first (top) endplate 302 presses against an anatomical structure (e.g. vertebrae) of the patient and the bottom inferior surface of the second (bottom) endplate 304 presses against an opposing anatomical structure of the patient. The superior and/or inferior surfaces of the first (top) endplate 302 and second (bottom) endplate 304 that contact the anatomical structures of the patient may be referred to herein as bone contacting surfaces. These bone contacting surfaces may include, or be considered formed by, raised surface features 306 and/or embedded graft features 308 that promote or otherwise enhance bone growth on or in the implant 300. The raised surface features 306 along the top and bottom surfaces of implant 300, which may also be referred to herein as undulations, provide more surface area than a flat surfaced implant and therefore additional bone growth surfaces. In addition, it should be understood that surface features 30 may include peaks and valleys, and the peaks may penetrate the adjacent VB, therefore compressing the immediately adjacent bone, providing compressed, denser bone for mating with the implant. The raised surface features and/or embedded graft features will be described in more detail in reference to the remaining drawings.

Figure 4A:
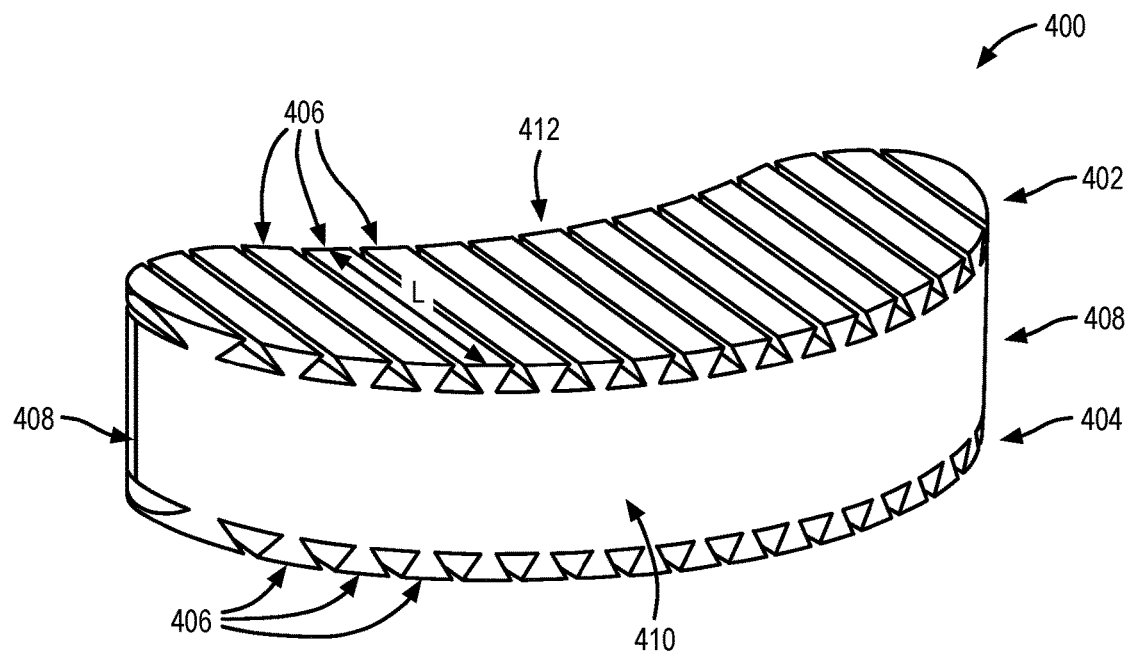
FIG. 4A shows a perspective view of one aspect of an interbody spinal implant.

In another aspect, the implant may be a non-expandable or non-adjustable interbody device as shown in FIG. 4A. Representatively, in one aspect, implant 400 may be a unibody cage. In this aspect, implant 400 may include a first (top) side 402 connected to a second (bottom) side 404 by lateral sides 408. Implant 400 may further include an anterior side 410 and a posterior side 412. In some aspects, the lateral side 408, anterior side 410 and/or posterior side 412 alone, or in combination, may also be referred to herein as a connector, a body, a column, or any other structure suitable for connecting first (top) side 402 to second (bottom) side 404. Unlike the previous configuration, the first (top) side 402 and the second (bottom) side 404 are fixed relative to one another and do not expand, or otherwise adjust, relative to one another.

In some aspects, the first (top) side 402 may be considered or referred to herein as a superior side of the implant 400 because it faces toward the head end of the body when inserted in the body. The second (bottom) side 404 may be considered or referred to herein as an inferior side of the implant because it faces away from the head when implant 400 is inserted in the body. In addition, the lateral sides 408 may face away from the midline (or middle) toward a side of the body, the anterior side 410 faces toward the front of the body (or is anterior to the posterior side 412), and the posterior side 412 faces toward the back of the body (or is posterior to the anterior side 410). In this aspect, when implant 400 is inserted in the body, the top or superior surface of first (top) side 402 presses against an anatomical structure (e.g. vertebrae) of the patient and the bottom inferior surface of the second (bottom) side 404 presses against an opposing anatomical structure of the patient. The superior and/or inferior surfaces of the first (top) side 402 and second (bottom) side 404 that contact the anatomical structures of the patient may therefore be referred to herein as bone contacting surfaces. These bone contacting surfaces may include, or be considered formed by, raised surface features 406 that increase a bone contacting surface area and/or enhance bone growth on or in the implant 400. In some aspects, raised surface features 406 may have a uniform size and shape such that they are all substantially the same. In still further aspects, surface features 406 may be arranged in a pattern, or so that they repeat in a uniform and continuous manner. Representatively, in one aspect, surface features 406 may be considered to be arranged in a linear pattern. In the illustrated configuration, surface features 406 are elongated continuous structures having a length dimension (L) that extends from anterior side 410 to posterior side 412 of implant 400. Surface features 406 may be arranged in a pattern in which their length dimensions (L) run parallel to one another. In some aspects, this arrangement of surface features 406 may be considered a linear pattern.

Figure 4B:
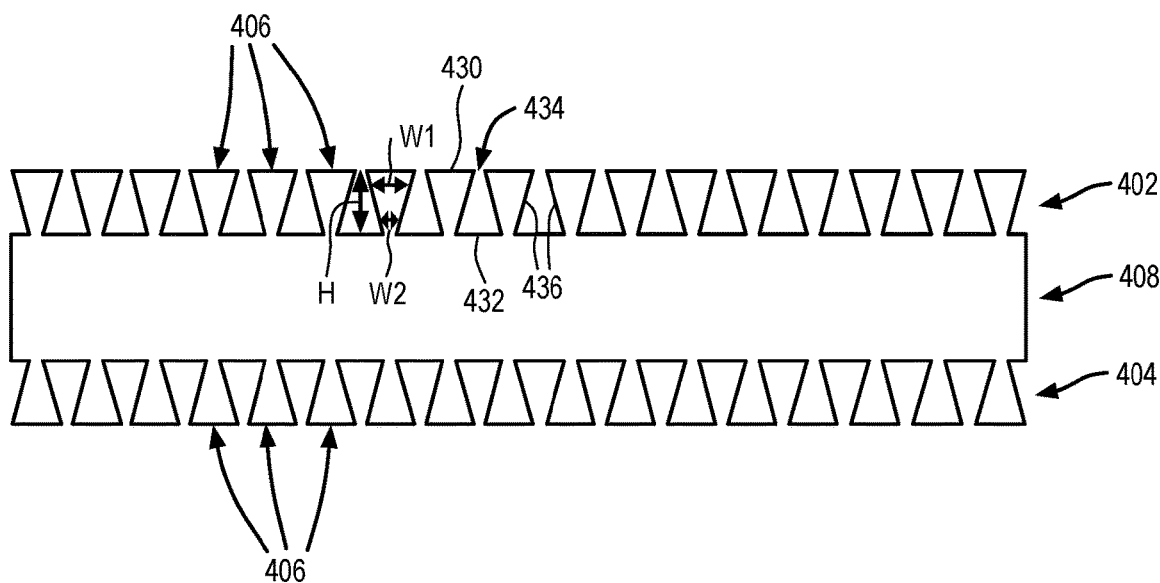
FIG. 4B shows a magnified cross-sectional side view of one aspect of the interbody spinal implant of FIG. 4A.

FIG. 4B illustrates a magnified cross-sectional side view of a portion of implant 400 having raised surface features 406. From this view, it can be seen that each of surface features 406 have a same cross sectional size and shape. Representatively, each of surface features 406 extend outward from the first and second sides 402, 404 to a peak 430. In this aspect, each of surface features 406 may therefore be considered as having a height (H) which may be defined by a distance from the base to the peak 430 of each of the surface features 406. In some aspects, the peak 430 of each of the surface features may be planar, or substantially planar, as shown. In still further aspects, a height (H) of each of surface features 406 may be the same, or substantially the same, such that they are considered coplanar with one another. In addition, in some aspects, each of surface features 406 may be undercut such that they have a substantially triangular shape as shown.

Representatively, peak 430 may form the base of the triangular shape and have a first width (W1) which is larger than a second width (W2) closer to the implant surface. Each of surface features 406 may be separated from adjacent surface features 406 by a trough, recess, groove or channel 432 defining a gap 434 in between each peak 430. The channel 432 may be defined by the side walls 436 of adjacent surface features 406. As a result of the shape of the surface features 406, the surface area of implant 400 is increased resulting in a greater surface area for bone growth in or on the implant 400. It should further be understood that although surface features 406 are shown on only the superior and inferior sides 402, 404 of implant 400, they could be formed on any side of the implant to enhance bone growth on or in the implant 400. In addition, although surface features 406 are shown on a unibody implant, it should be understood that surface features 406 may be applied to any interbody device (e.g., an expandable cage) or device in general having a bone contacting surface in which enhanced bone growth on or in the implant is desired. The troughs or channels 432 may be dimensioned to provide: (1) a substantial surface for bearing loading of the adjacent VBs; and (2) significant surface area for bone to grow into and onto. In this way, the troughs or channels 432 may be considered more friendly to bone than upward-opening troughs of device 300.

Figure 5A:
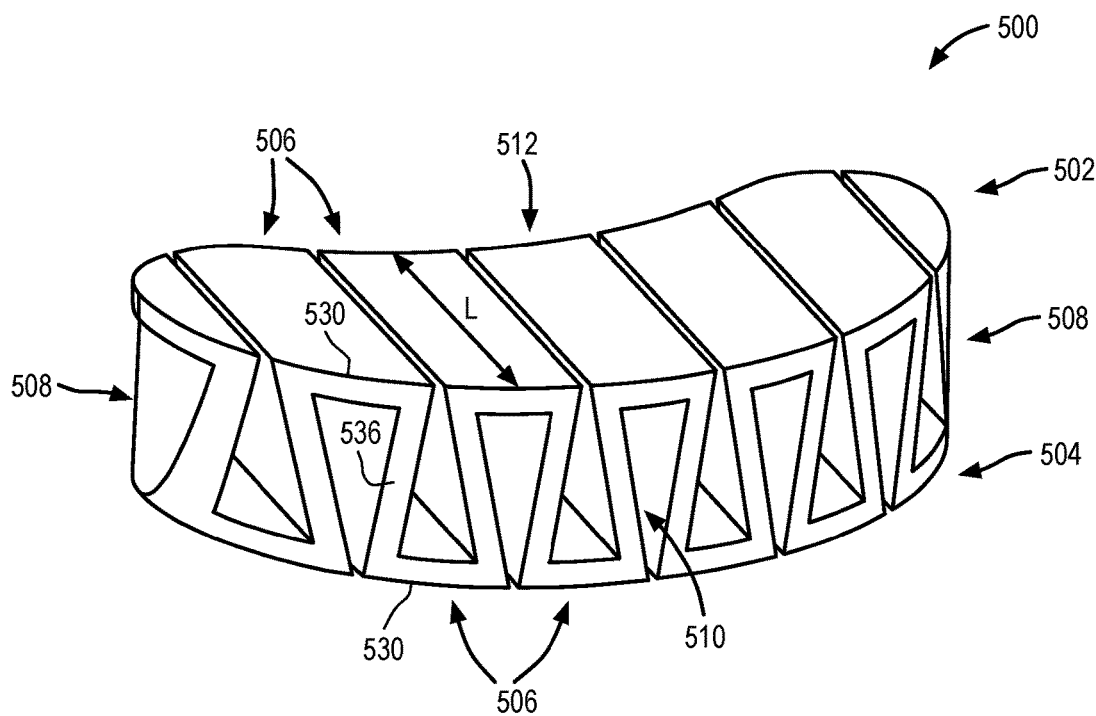
FIG. 5A shows a perspective view of one aspect of an interbody spinal implant.
Figure 5B:
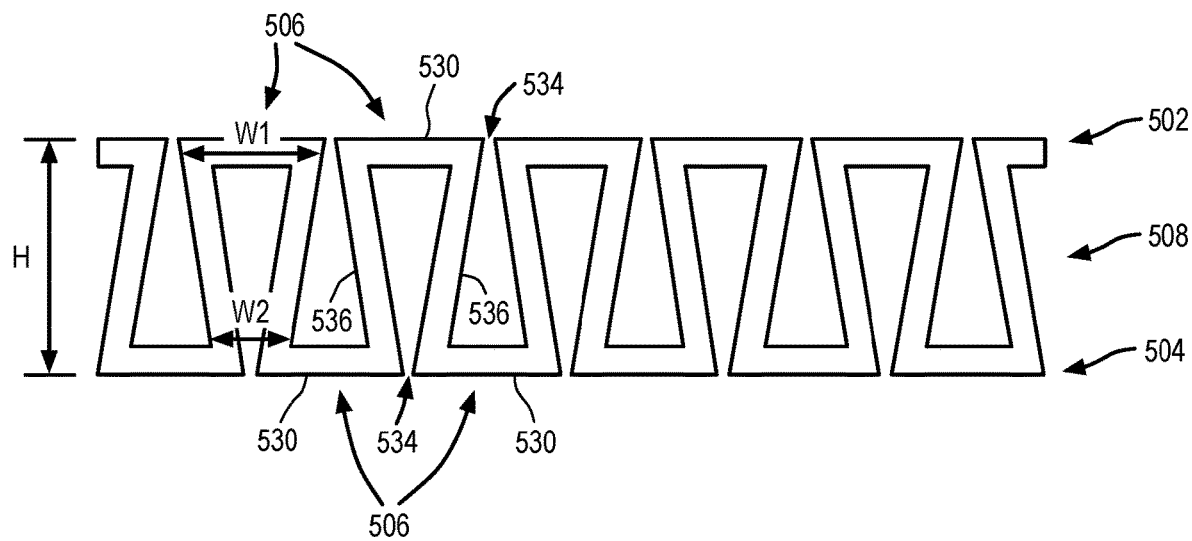
FIG. 5B shows a magnified cross-sectional side view of one aspect of the interbody spinal implant of FIG. 5A.

Referring now to FIG. 5A and FIG. 5B, FIGS. 5A-B illustrate another aspect of an implant having surface features. Representatively, implant 500 is substantially similar to implant 400 in that it may be a unibody cage including a first (top) side 502, a second (bottom) side 504, lateral sides 508, an anterior side 510 and a posterior side 512. In some aspects, the lateral sides 508, anterior side 510 and/or posterior side 512 alone, or in combination, may also be referred to herein as a connector, a body, a column, or any other structure suitable for connecting first (top) side 502 to second (bottom) side 504. In some aspects, the first (top) side 502 may be considered or referred to herein as a superior side of the implant and the second (bottom) side 504 may be considered or referred to herein as an inferior side of the implant. In this aspect, when implant 500 is inserted in the body, the top or superior surface of first (top) side 502 presses against an anatomical structure (e.g. vertebrae) of the patient and the bottom inferior surface of the second (bottom) side 504 presses against an opposing anatomical structure of the patient. The superior and/or inferior surfaces of the first (top) side 502 and second (bottom) side 504 that contact the anatomical structures of the patient may therefore be considered bone contacting surfaces and include raised surface features 506 that increase a bone contacting surface area and/or enhance bone growth on or in the implant 500.

In some aspects, raised surface features 506 may be similar to the previously discussed surface features in that they have a uniform size and shape, and are arranged in a pattern, or so that they repeat in a uniform and continuous manner. Representatively, in one aspect, surface features 506 may be considered to be arranged in a linear pattern. In the illustrated configuration, surface features 506 are elongated continuous structures having a length dimension (L) that extends from anterior side 510 to posterior side 512 of implant 500. Surface features 506 may be arranged in a pattern in which their length dimensions (L) run parallel to one another. In addition, surface features 506 may have substantially flat peaks 530 and an undercut such that they have a substantially triangular shape. Representatively, peak 530 may form the base of the triangular shape and have a first width (W1) which is larger than a second width (W2). Each of surface features 506 may be separated from adjacent surface features 506 by a trough, recess, groove or channel defining a gap 534 in between each peak 530.

In this configuration, however, surface features 506 are considered overlapping in that they extend all the way through the implant from the first (top) side 502 to the second (bottom) side 504. Representatively, as can be seen from the magnified cross-sectional side view of FIG. 5B, surface features have a height (H) which corresponds to a distance between the first (top) side 502 and the second (bottom) side 504. The trough, recess, groove or channel of the surface features 506 on the first (top) side 502 is therefore defined by the interior surfaces of the side walls 536 of surface features 506 at the second (bottom) side 504. Similarly, the trough, recess, groove or channel of the surface features 506 at the second (bottom) side 504 is defined by the interior surfaces of the side walls 536 of surface features 506 at the first (top) side 502. In some aspects, the height (H) of each of the surface features 506 may be the same, or substantially the same such that all the peaks 530 are coplanar. In addition, the peak 530 of each of the surface features 506 may be planar, or substantially planar, as shown. As a result of the shape of the surface features 506, the surface area of implant 500 is increased resulting in a greater surface area for bone growth in or on the implant 500. It should further be understood that although surface features 506 are shown on only the superior and inferior sides 502, 504 of implant 500, they could be formed on any side of the implant to enhance bone growth on or in the implant 500. In addition, although surface features 506 are shown on a unibody implant, it should be understood that surface features 506 may be applied to any interbody device (e.g., an expandable cage) or device in general having a bone contacting surface in which enhanced bone growth on or in the implant is desired. It should further be understood that implant 500 is similar to the undercut features of implant 400, but taken to the extreme to maximize internal volume available for bone to grow onto and into. It may be understood that the cross sections provided would be the minimum thickness to support surgical loading in an effort to maximize the troughs between superior and inferior sides 502, 504. It should further be understood that peaks 530 may have holes (not shown) in them to allow any graft growing into trough 510 to access the other side and vice versa, and further increasing surface area for bone to grow onto and into.

Figure 6A:
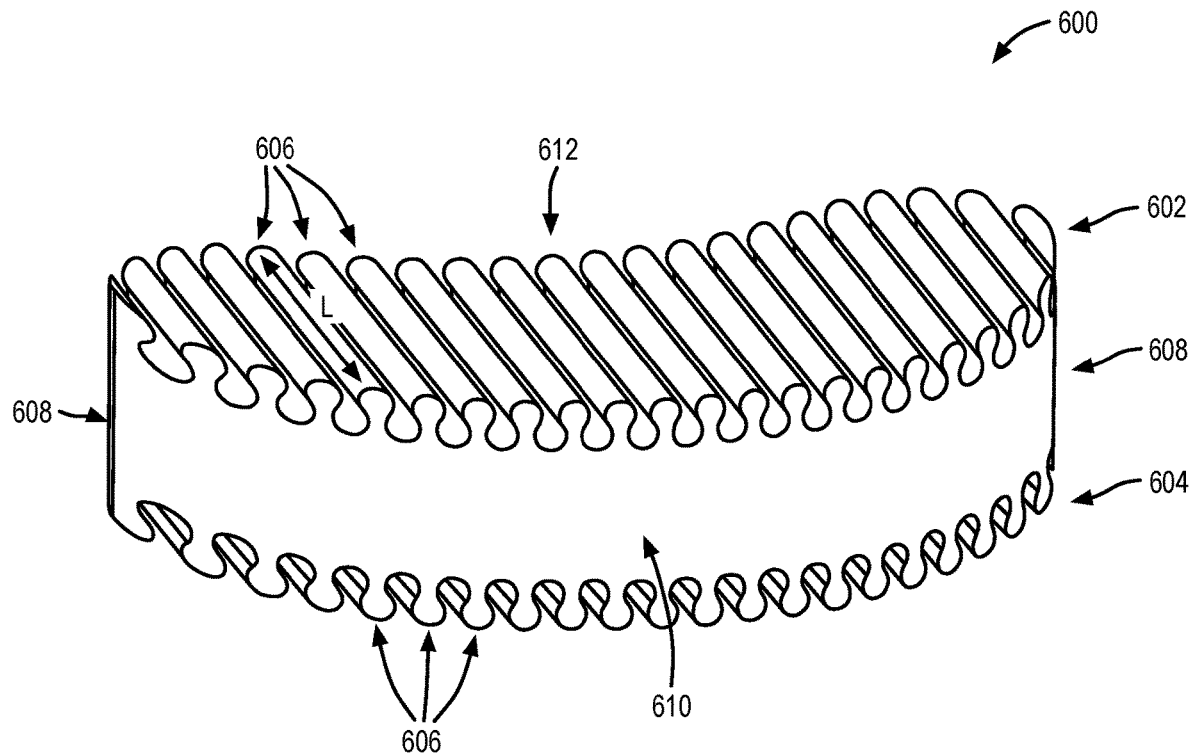
FIG. 6A shows a perspective view of one aspect of an interbody spinal implant.
Figure 6B:
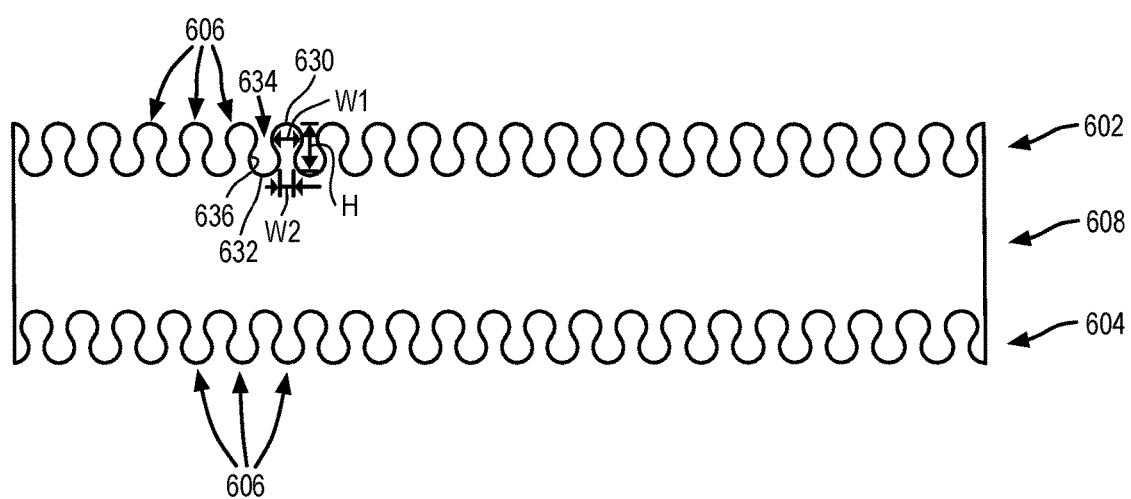
FIG. 6B shows a magnified cross-sectional side view of one aspect of the interbody spinal implant of FIG. 6A.

Referring now to FIG. 6A and FIG. 6B, FIGS. 6A-B illustrates another aspect of an implant having surface features. Representatively, implant 600 is substantially similar to the previously discussed implants in that it may be a unibody cage including a first (top) side 602, a second (bottom) side 604, lateral sides 608, an anterior side 610 and a posterior side 612. In some aspects, the lateral sides 608, anterior side 610 and/or posterior side 612 alone, or in combination, may also be referred to herein as a connector, a body, a column, or any other structure suitable for connecting first (top) side 602 to second (bottom) side 604. In some aspects, the first (top) side 602 may be considered or referred to herein as a superior side of the implant and the second (bottom) side 604 may be considered or referred to herein as an inferior side of the implant. In this aspect, when implant 600 is inserted in the body, the top or superior surface of first (top) side 602 presses against an anatomical structure (e.g. vertebrae) of the patient and the bottom inferior surface of the second (bottom) side 604 presses against an opposing anatomical structure of the patient. The superior and/or inferior surfaces of the first (top) side 602 and second (bottom) side 604 that contact the anatomical structures of the patient may therefore be considered bone contacting surfaces and include raised surface features 606 that increase a bone contacting surface area and/or enhance bone growth on or in the implant 600.

In some aspects, raised surface features 606 may be similar to the previously discussed surface features in that they have a uniform size and shape, and are arranged in a pattern, or so that they repeat in a uniform and continuous manner. Representatively, in one aspect, surface features 606 may be considered to be arranged in a linear pattern. In the illustrated configuration, surface features 606 are elongated continuous structures having a length dimension (L) that extends from anterior side 610 to posterior side 612 of implant 600. Surface features 606 may be arranged in a pattern in which their length dimensions (L) run parallel to one another.

In this configuration, however, surface features 606 may have substantially round peaks 630 such that they have a substantially round or tear drop shape. In this aspect, surface features 606 may be considered arranged in an undulating pattern or configuration. In still further aspects, a height (H) of each of surface features 606 may be the same, or substantially the same, such that they are considered coplanar with one another. In addition, in some aspects, each of surface features 606 may be undercut or otherwise cut inward such that they are narrower at one end than the other.

Representatively, as can be seen from the magnified view of the surface features found in FIG. 6B, peak 630 may be round and have a first width (W1) which is larger than a second width (W2) closer to the implant surface. Each of surface features 606 may be separated from adjacent surface features 606 by a trough, recess, groove or channel 632 defining a gap 634 in between each peak 630. The channel 632 may be defined by the side walls 636 of adjacent surface features 606. As a result of the shape of the surface features 606, the surface area of implant 600 is increased resulting in a greater surface area for bone growth in or on the implant 600. It should further be understood that although surface features 606 are shown on only the superior and inferior sides 602, 604 of implant 600, they could be formed on any side of the implant to enhance bone growth on or in the implant 600. In addition, although surface features 606 are shown on a unibody implant, it should be understood that surface features 606 may be applied to any interbody device (e.g., an expandable cage) or device in general having a bone contacting surface in which enhanced bone growth on or in the implant is desired. It should further be understood that surface features 606 may be smoother on the surfaces that interact with bone, therefore causing less trauma and subsidence. Surface features 606 may also be configured to maximize the speed of bone growth and/or to maximize surface area as compared to substantially flat surfaces with devices 400 or 500. Representatively, the curvature of surface features 606 could be maximized based on the body's natural growth rate such that the curves steepen where the bone grows faster and shallow in places where the bone may grow slower).

Figure 7A:
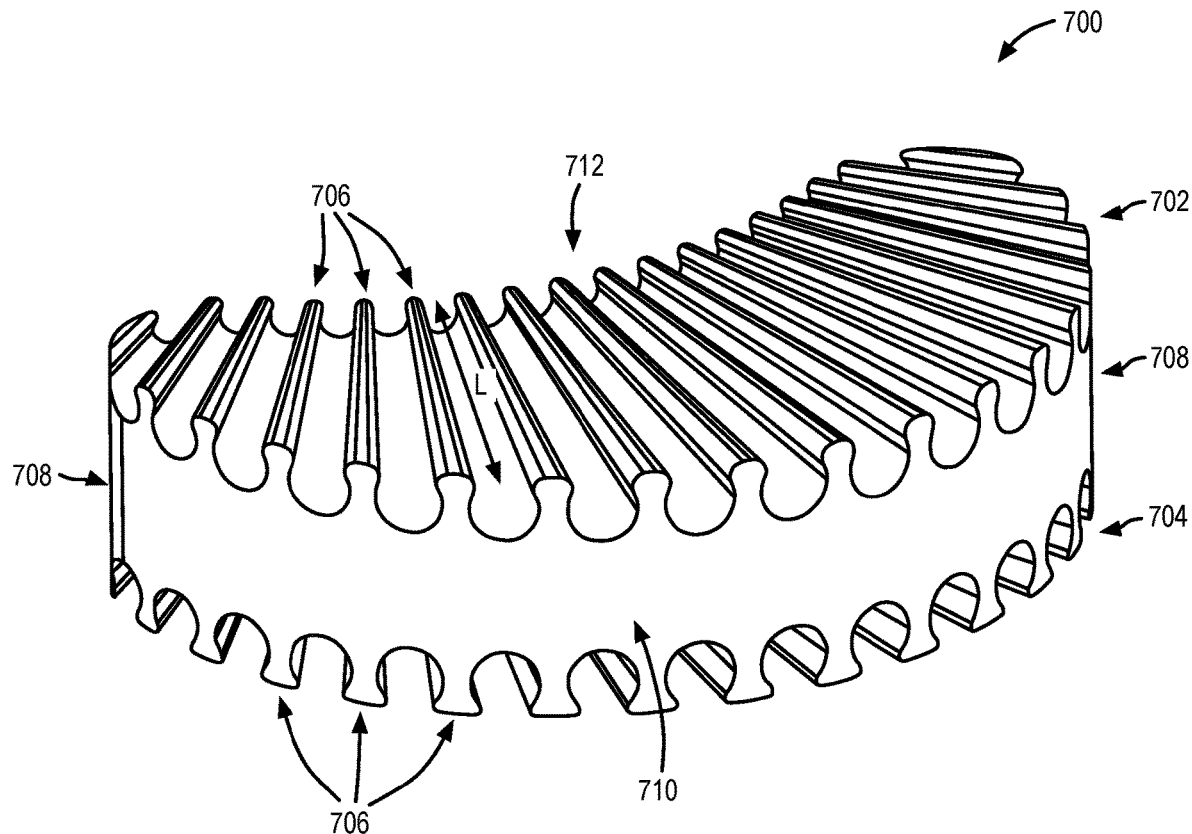
FIG. 7A shows a perspective view of one aspect of an interbody spinal implant.
Figure 7B:
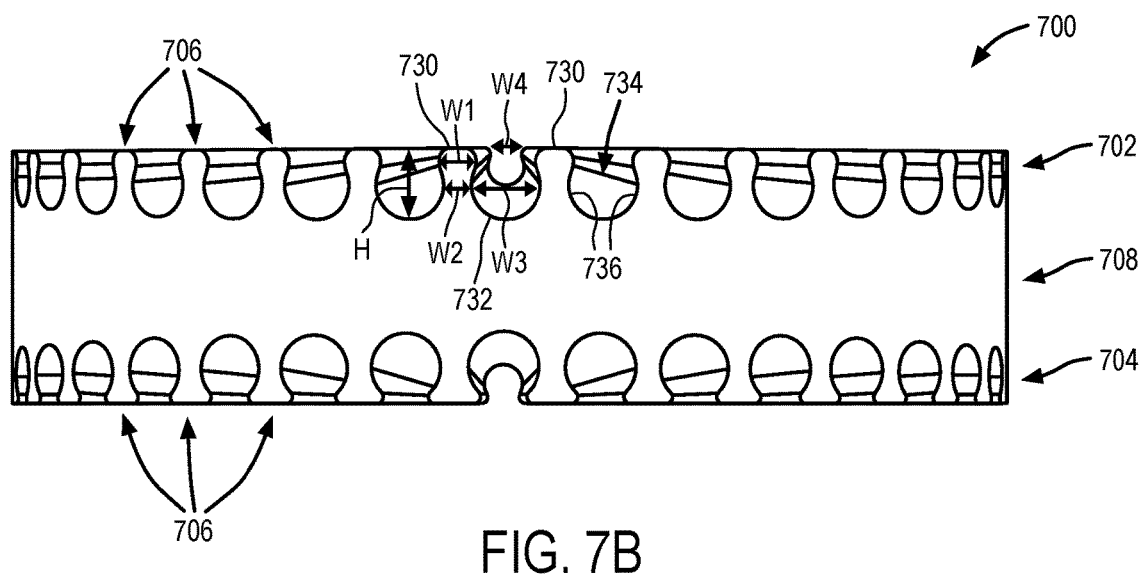
FIG. 7B shows a magnified cross-sectional side view of one aspect of the interbody spinal implant of FIG. 7A.

Referring now to FIG. 7A and FIG. 7B, FIGS. 7A-B illustrates another aspect of an implant having surface features. Representatively, implant 700 is substantially similar to the previously discussed implants in that it may be a unibody cage including a first (top) side 702, a second (bottom) side 704, lateral sides 708, an anterior side 710 and a posterior side 712. In some aspects, the lateral sides 708, anterior side 710 and/or posterior side 712 alone, or in combination, may also be referred to herein as a connector, a body, a column, or any other structure suitable for connecting first (top) side 702 to second (bottom) side 704. In some aspects, the first (top) side 702 may be considered or referred to herein as a superior side of the implant and the second (bottom) side 704 may be considered or referred to herein as an inferior side of the implant. In this aspect, when implant 700 is inserted in the body, the top or superior surface of first (top) side 702 presses against an anatomical structure (e.g. vertebrae) of the patient and the bottom inferior surface of the second (bottom) side 704 presses against an opposing anatomical structure of the patient. The superior and/or inferior surfaces of the first (top) side 702 and second (bottom) side 704 that contact the anatomical structures of the patient may therefore be considered bone contacting surfaces and include raised surface features 706 that increase a bone contacting surface area and/or enhance bone growth on or in the implant 700.

In some aspects, raised surface features 706 may be similar to the previously discussed surface features in that they have a uniform size and shape, and are arranged in a pattern, or so that they repeat in a uniform and continuous manner. Representatively, surface features 706 may have substantially smooth or round peaks 730 such that they have a substantially round or tear drop shape. In still further aspects, a height (H) of each of surface features 706 may be the same, or substantially the same, such that they are considered coplanar with one another. In addition, in some aspects, each of surface features 706 may be undercut or otherwise cut inward such that they are narrower at one end than the other. Representatively, as can be seen from the magnified view of the surface features found in FIG. 7B, peak 730 may be round and have a first width (W1) which is larger than a second width (W2) closer to the implant surface. Each of surface features 706 may be separated from adjacent surface features 706 by a trough, recess, groove or channel 732 defining a gap 734 in between each peak 730. The channel 732 may be defined by the side walls 736 of adjacent surface features 706.

In implant 700, however, the surface features 706 are arranged such that they radiate outward along the first (top) side 702 and/or second (bottom) side 704. In other words, the length dimension (L) of the surface features 706 radiates outward from the posterior side 712 to the anterior side 710. In another aspect, the length dimension (L) of surface features 706 could radiate in a different direction, or from a different point, such as the middle of the cage, or possibly from one side to another laterally. As a result, the channel 732 formed between each of the surface features 706 has a different width (W3) at the anterior side 710 than the width (W4) at the posterior side 712. Representatively, the width (W3) of channel 732 at the anterior side 710 may be wider than the width (W4) at the posterior side 712. Said another way, the channel 732 has a tapered width that narrows in the direction of the posterior side 712, or widens in the direction of the anterior side 710. As a result of the shape of the surface features 706, the surface area of implant 700 is increased resulting in a greater surface area for bone growth in or on the implant 700. It should further be understood that although surface features 706 are shown on only the superior and inferior sides 702, 704 of implant 700, they could be formed on any side of the implant to enhance bone growth on or in the implant 700. In addition, although surface features 706 are shown on a unibody implant, it should be understood that surface features 706 may be applied to any interbody device (e.g., an expandable cage) or device in general having a bone contacting surface in which enhanced bone growth on or in the implant is desired. It may further be understood that the raised surface features 706 may not be agnostic of the cage shape, as with 400, 500 and 600, but instead may be directional relative to the cage shape, which may benefit bony on/ingrowth, as well as subside less. In addition, the cross section of the troughs or channels 732 can change in accordance with what is needed from the design.

Figure 8A:
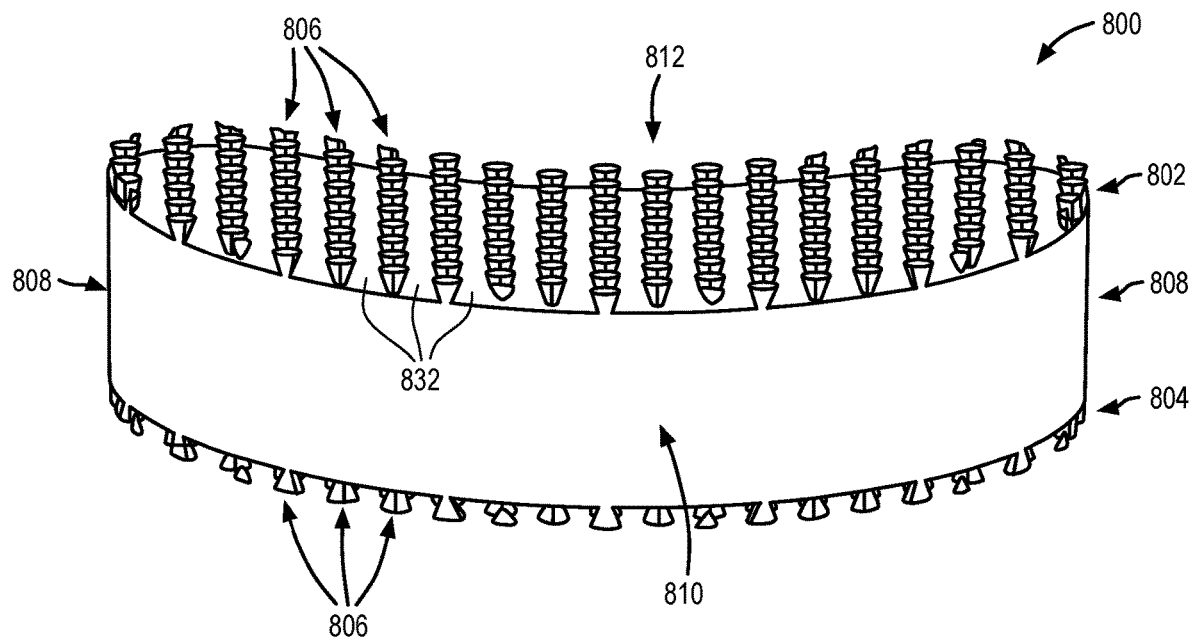
FIG. 8A shows an anterior perspective view of one aspect of an interbody spinal implant.
Figure 8B:
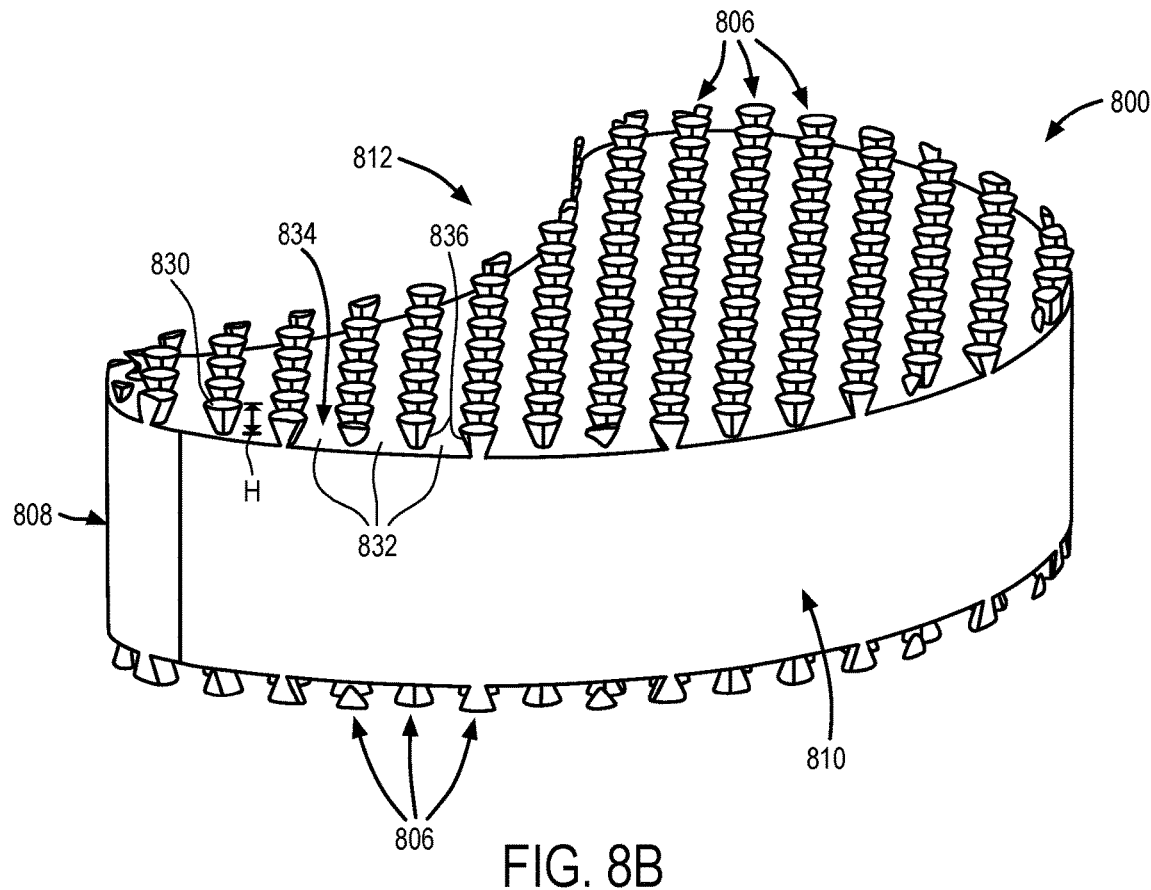
FIG. 8B shows a lateral perspective view of the interbody spinal implant of FIG. 6A.

Referring now to FIG. 8A and FIG. 8B, FIGS. 8A-B illustrates another aspect of an implant having surface features. Representatively, implant 800 is substantially similar to the previously discussed implants in that it may be a unibody cage including a first (top) side 802, a second (bottom) side 804, lateral sides 808, an anterior side 810 and a posterior side 812. In some aspects, the lateral sides 808, anterior side 810 and/or posterior side 812 alone, or in combination, may also be referred to herein as a connector, a body, a column, or any other structure suitable for connecting first (top) side 802 to second (bottom) side 804. In some aspects, the first (top) side 802 may be considered or referred to herein as a superior side of the implant and the second (bottom) side 804 may be considered or referred to herein as an inferior side of the implant. In this aspect, when implant 800 is inserted in the body, the top or superior surface of first (top) side 802 presses against an anatomical structure (e.g. vertebrae) of the patient and the bottom inferior surface of the second (bottom) side 804 presses against an opposing anatomical structure of the patient. The superior and/or inferior surfaces of the first (top) side 802 and second (bottom) side 804 that contact the anatomical structures of the patient may therefore be considered bone contacting surfaces and include raised surface features 806 that increase a bone contacting surface area and/or enhance bone growth on or in the implant 800.

In some aspects, raised surface features 806 may be similar to the previously discussed surface features in that they have a uniform size and shape, and are arranged in a pattern, or so that they repeat in a uniform and continuous manner. In the illustrated configuration, however, surface features 806 are discrete structures that extend from the first (top) side 802 and second (bottom) side 804 of implant 600. Representatively, surface features 806 may be a series of undercut structures that are arranged in linear rows and superimposed on each other to form a linear pattern of features 806 when viewed from the anterior side 810 as shown in FIG. 8A, and the lateral side 808 as shown in FIG. 8B.

Each of the discrete surface features 806 may have substantially flat or planar peaks 830. In still further aspects, a height (H) of each of surface features 806 may be the same, or substantially the same, such that they are considered coplanar with one another. In addition, each of surface features 806 may be undercut or otherwise cut inward such that they are narrower at one end (e.g., top end) than the other (e.g., bottom end). For example, surface features 806 may have a substantially triangular cross-sectional shape, or an overall pyramid like shape. Each of surface features 806 may be separated on all sides from adjacent surface features 806 by a trough, recess, groove or channel 832 defining a gap 834 in between each peak 830. The channel 832 may be defined by the side walls 836 of adjacent surface features 806. As can be seen from the anterior and lateral side views shown in FIG. 8A and FIG. 8B respectively, channels 832 separate the surface features 806 on all sides. As a result of the shape of the surface features 806, the surface area of implant 800 is increased resulting in a greater surface area for bone growth in or on the implant 800. It should further be understood that although surface features 806 are shown on only the superior and inferior sides 802, 804 of implant 800, they could be formed on any side of the implant to enhance bone growth on or in the implant 800. In addition, although surface features 806 are shown on a unibody implant, it should be understood that surface features 806 may be applied to any interbody device (e.g., an expandable cage) or device in general having a bone contacting surface in which enhanced bone growth on or in the implant is desired.

Figure 9A:
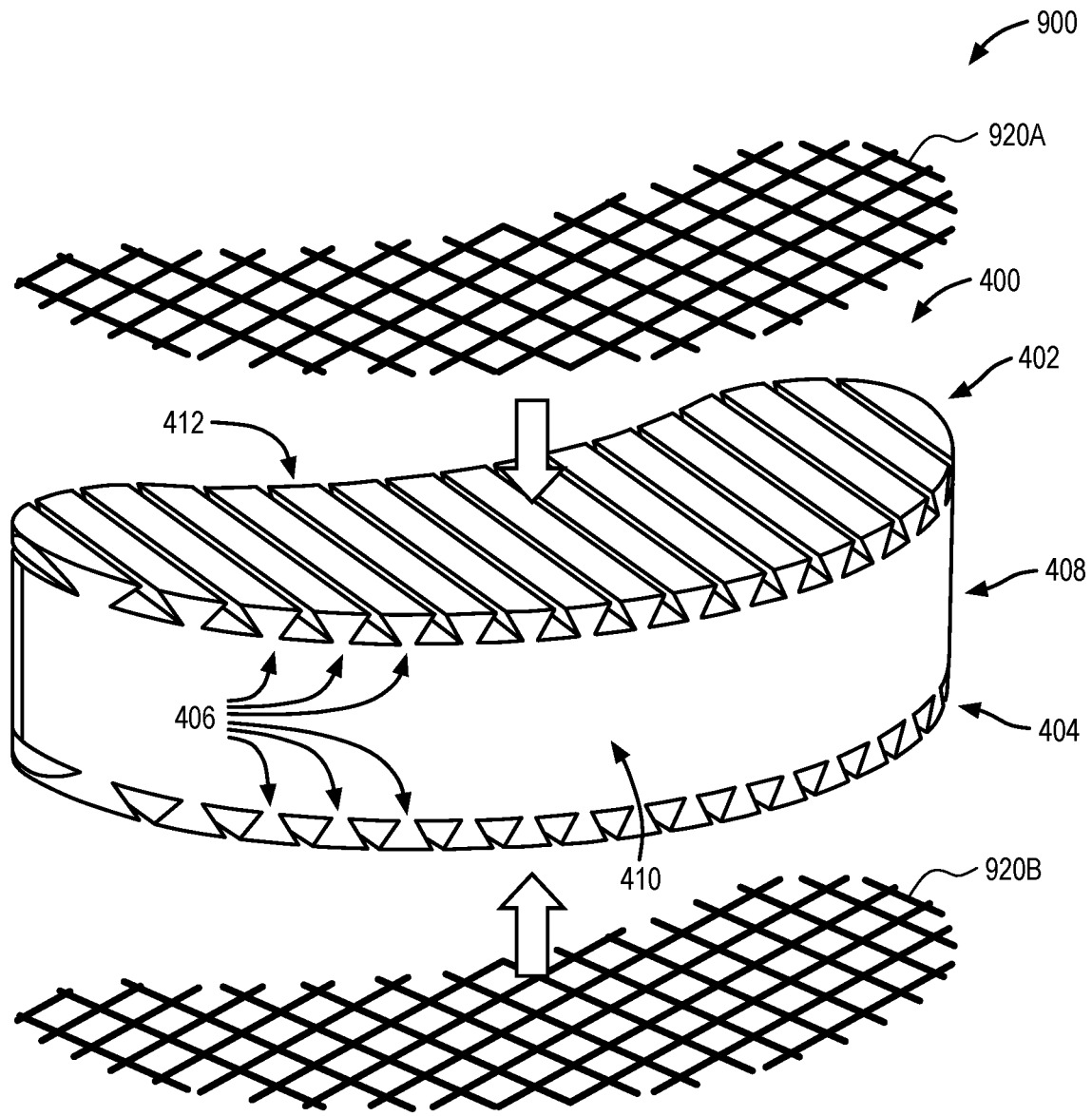
FIG. 9A shows a perspective view of one aspect of an interbody spinal implant.
Figure 9B:
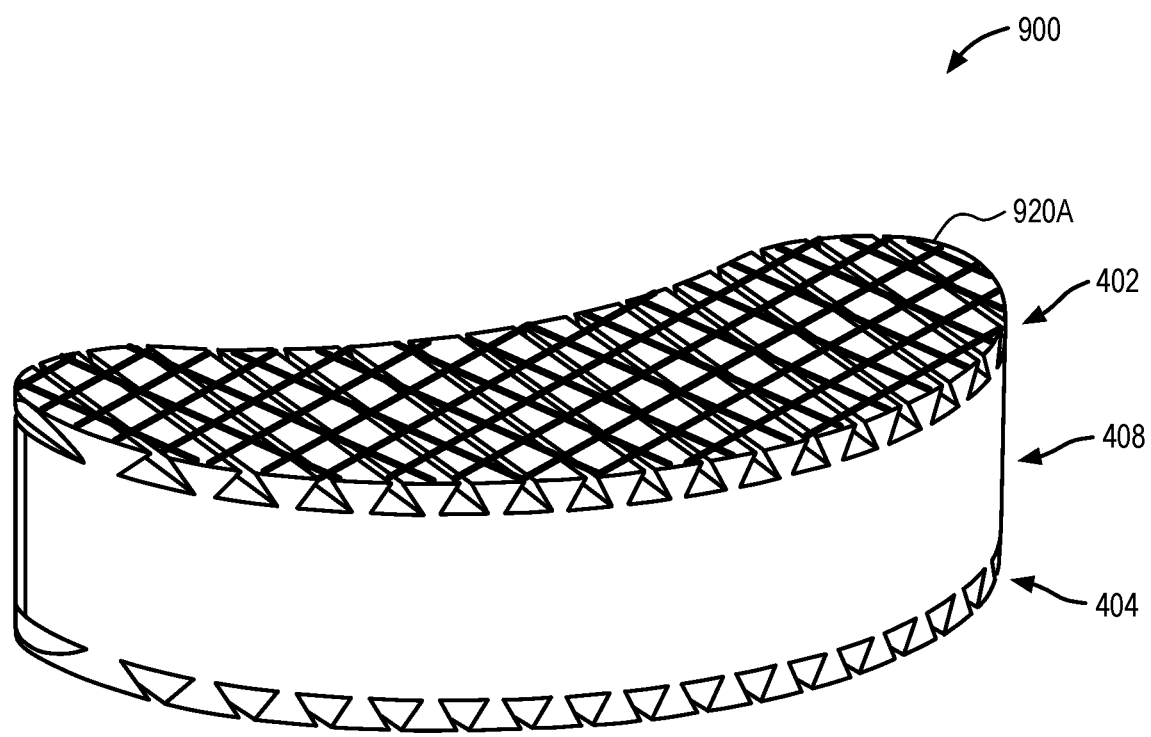
FIG. 9B shows a further perspective view of the interbody spinal implant of FIG. 9A.

Referring now to FIG. 9A and FIG. 9B, FIGS. 9A-B illustrate another aspect of an implant having surface features. Representatively, implant 400 is implant 400 previously discussed in reference to FIGS. 4A-B, and includes first (top) side 402, second (bottom) side 404, lateral sides 408, anterior side 410, posterior side 412 and surface features 406 formed on the first and second sides 402, 404 that form the bone contacting surfaces. In addition to surface features 406 to promote bone growth on or in implant 400, implant 400 may further include mesh layers 920A, 920B coupled to the sides 402, 404. The mesh layers 920A, 920B may be coupled to surface features 406 and be configured to further increase the surface area. Representatively, in one aspect, mesh layers 920A-B may be welded or otherwise attached to the top (or peaks) of surface features 406 as shown in FIG. 9B. Mesh layers 920A-B may be formed of a mesh material (e.g., woven material, or a perforated sheet) that could be the same or different than the material used to form implant 400. The web like pattern or construction of the material used to form the mesh layers 920A-B provides additional surface structures and therefore surface area for attachment of bone on or in the implant 400. It should further be understood that although mesh layers 920A-B are shown on only the superior and inferior sides 402, 404 of implant 400, they could be attached to any side of the implant to enhance bone growth on or in the implant 400. In addition, although mesh layers 920A-B are shown on a unibody implant, it should be understood that they may be applied to any interbody device (e.g., an expandable cage) or device in general having a bone contacting surface in which enhanced bone growth on or in the implant is desired.

Figure 10A:
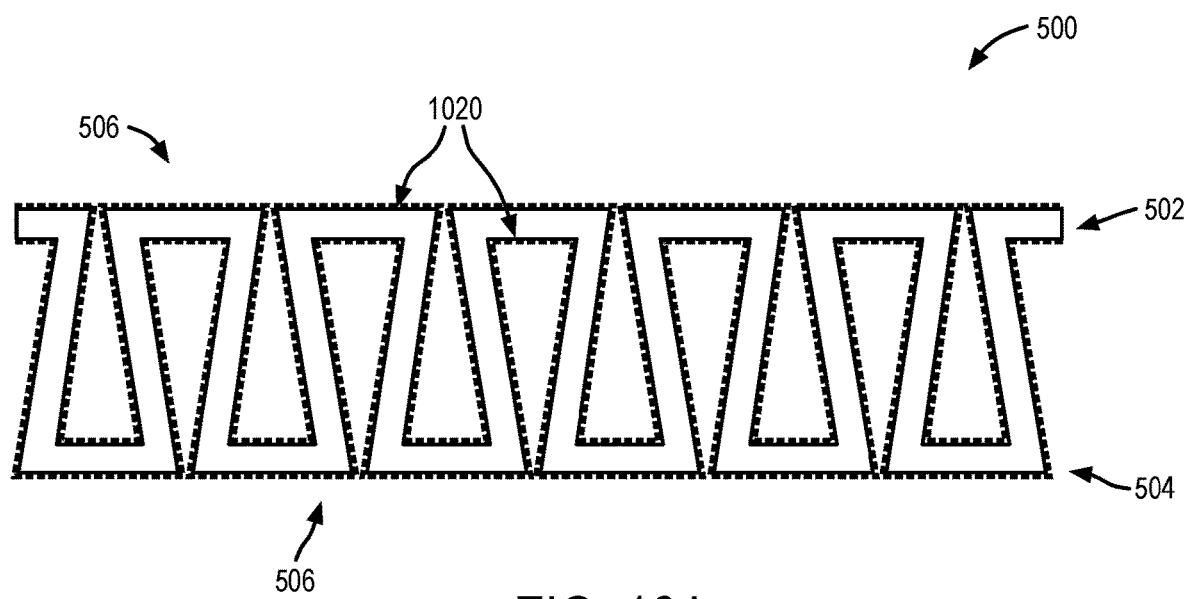
FIG. 10A shows a magnified cross-sectional side view of one aspect of an interbody spinal implant having a surface coating.
Figure 10B:
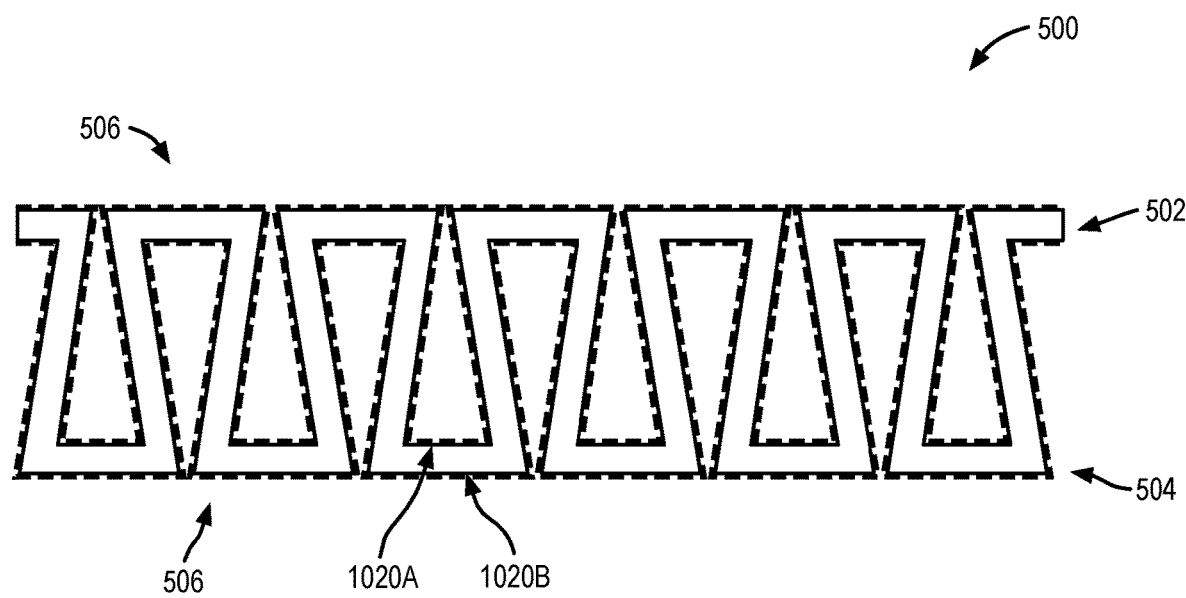
FIG. 10B shows a magnified cross-sectional side view of another aspect of an interbody spinal implant having a surface coating.

Referring now to FIG. 10A and FIG. 10B, FIGS. 10A-B illustrate another aspect of an implant having surface features. Representatively, FIGS. 10A-B show a cross-sectional magnified view of implant 500 as previously discussed in reference to FIGS. 5A-B, and including first (top) side 502, second (bottom) side 504, and overlapping surface features 506 extending from side 502 to side 504. In addition to surface features 506 to promote bone growth on or in implant 500, implant 500 may further include a surface coating 1020 applied to the surfaces of surface features 506 to further enhance bone growth on or in the implant. In some aspects, surface coating 1020 may be a uniform coating (e.g., same thickness and/or texture) applied to all surfaces of surface features 506 as shown in FIG. 10A. In other aspects, surface coating 1020 may be a non-uniform coating (e.g., different thicknesses and/or texture) applied to all surfaces of surface features 506 as shown in FIG. 10B. Representatively, as shown in FIG. 10B, surface coating 1020A formed on the surfaces facing the top side 502 of implant 500 has a first thickness or texture, and surface coating 1020B formed on the surfaces facing the bottom side 504 of implant 500 has a second thickness or texture that is different than the first thickness or texture. In some aspects, surface coating 1020A is thinner than surface coating 1020B. In other aspects, surface coating 1020A has a different texture, for example is less porous, than surface coating 1020B. Surface coating 1020 may be an additive coating applied by any suitable processing operation, for example, hydroxyapatite (HA) plasma spray coating, three-dimensional (3D) printing, laser welded beads or the like. In some aspects, surface coating 1020A may be made of the same material as surface coating 1020B. In other aspects, surface coating 1020A may be a different material than surface coating 1020B. In another aspect, the dotted lines on the surfaces of the parts could represent a subtractive process, such as an acid dip which would remove material, or a subtractive blasting technique such as sand blasting, which both would leave a rough, bone friendly surface.

Figure 11:
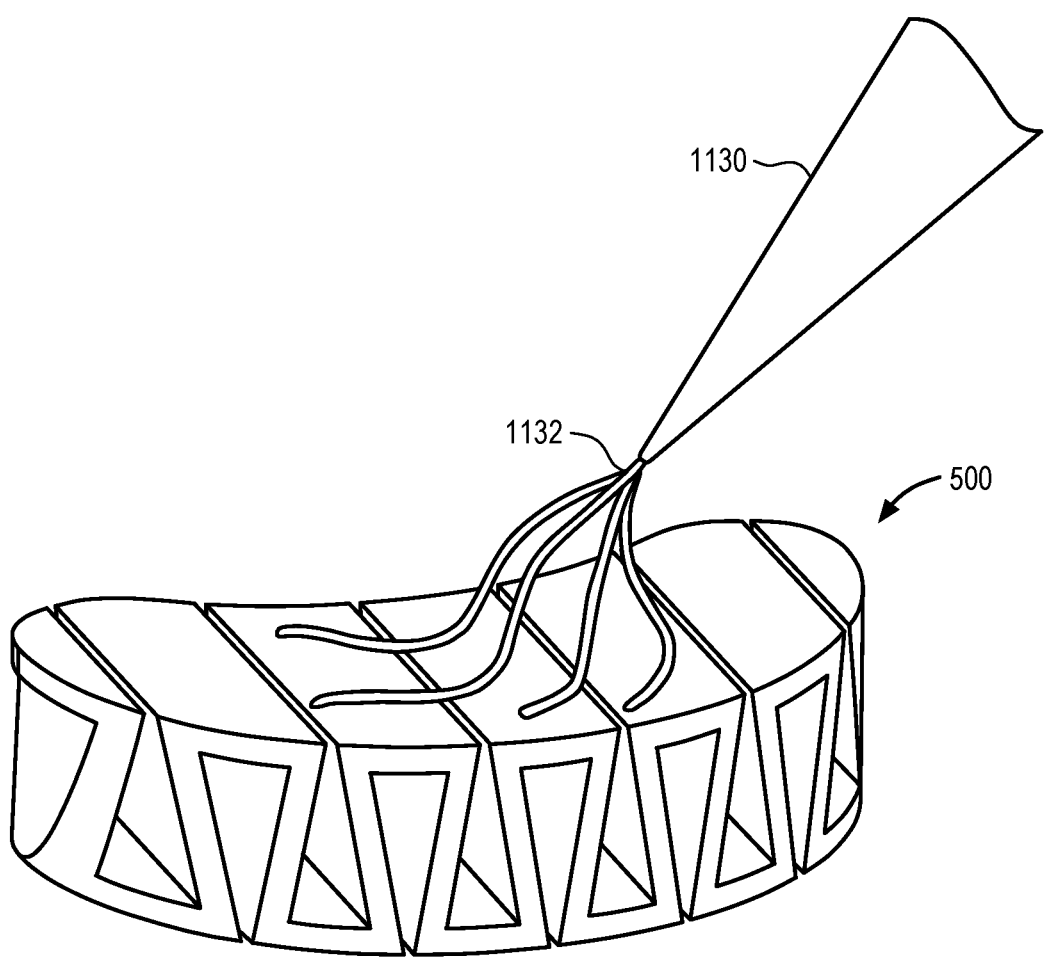
FIG. 11 shows a perspective view of an aspect of a processing operation for applying a surface coating to an interbody spinal implant.

FIG. 11 illustrates one representative process for applying coating 1020 to surface features 506. Representatively, in one aspect, surface coating 1020 may be applied by a nozzle 1130 configured to deposit, spray or otherwise apply the surface coating material 1132 (e.g., hydroxyapatite (HA)) to the surfaces of implant 500. It should further be understood that while FIG. 11 shows one representative process for applying a coating to implant 500, the same process could be used to apply a coating to any of the implant configurations disclosed herein.

Figure 12A:
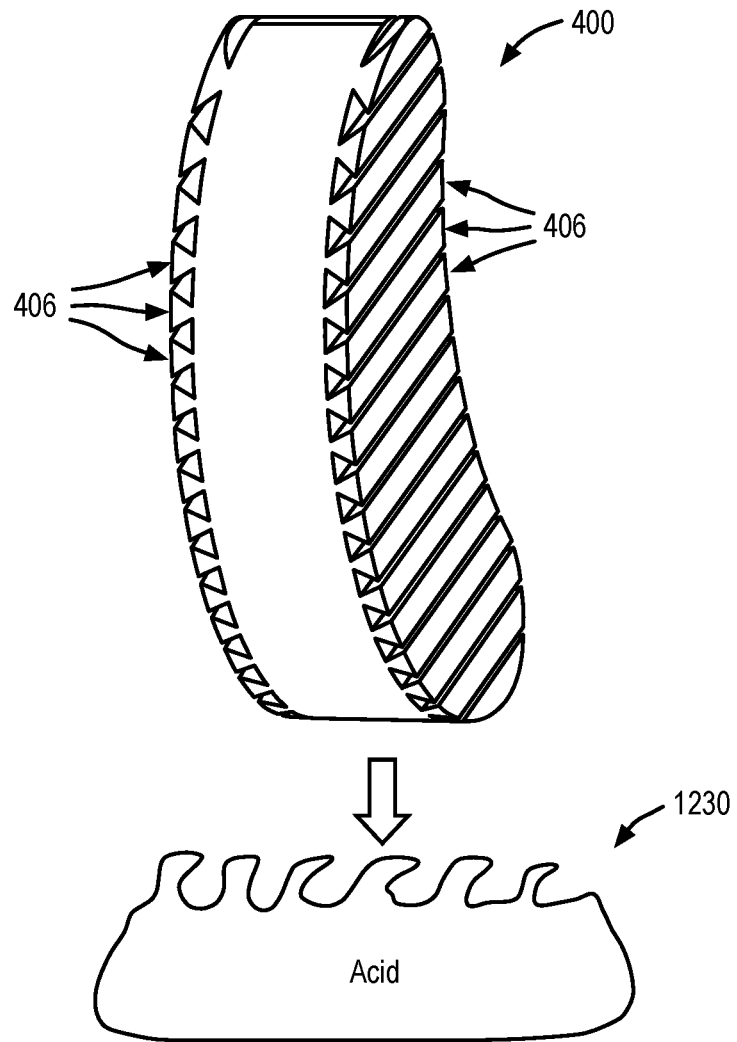
FIG. 12A shows a perspective view of an aspect of a processing operation for applying a surface texture to an interbody spinal implant.
Figure 12B:
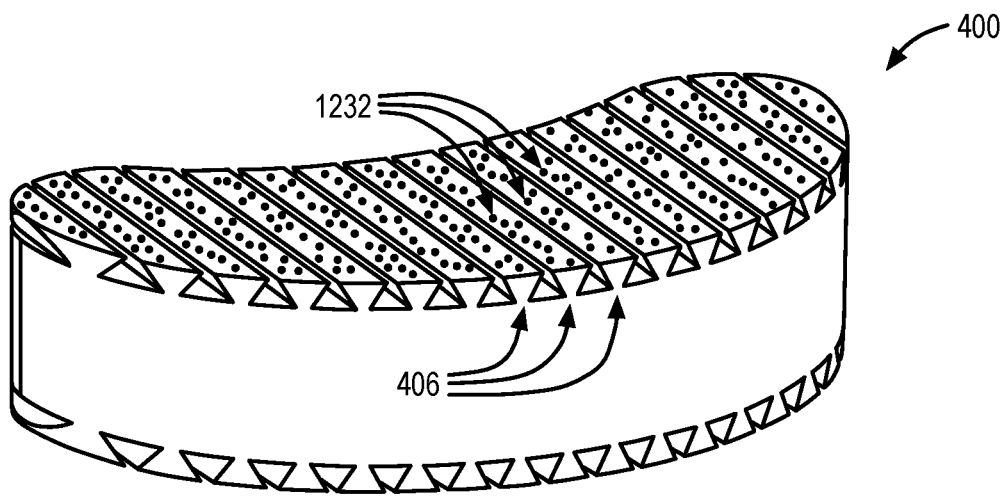
FIG. 12B shows a perspective view of the interbody spinal implant including the surface texture applied in FIG. 12A.

FIGS. 12A and 12B illustrate another representative process for increasing a surface area of any one or more of the previously discussed implants. For example, FIGS. 12A-B show a process for increasing a surface area of implant 400 previously discussed in reference to FIGS. 4A-B. Representatively, FIG. 12A illustrates a subtractive process in which implant 400 is dipped into an acid solution 1230 to form nano-scale texture or features 1232 on or in the surface features 406 that are favorable for growing bone. The nano-scale texture or features 1232 could be raised features that have a nano-scale roughness. Each roughness may comprise regular, irregular, or combinations of regular and irregular structural features, e.g., the nano-scale roughness may independently be regular, irregular, or both regular and irregular in terms of the structural arrangement of the surface. In one aspect, the nano-scale structures may have a maximum peak to valley height of from about 0.001 μm to about 20 μm. The implant 400 may remain in the acid solution 1230 for a sufficient amount of time to produce nano-scale surface texture or features 1232 on the surface features 406. In some aspects, the surface features 406 of implant 400 could be masked to allow application of different amounts of scoring/texturing features 1232 as desired. It should further be understood that while FIGS. 12A-B show one representative process for applying non-scale features or texture to implant 400, the same process could be used to apply nano-scale features or a texture to any of the implant configurations disclosed herein. It is also understood that, through masking, features such as troughs or channels (e.g., channels 432) could be formed using a subtractive technique, thereby maximizing the available surface.

Figure 13A:
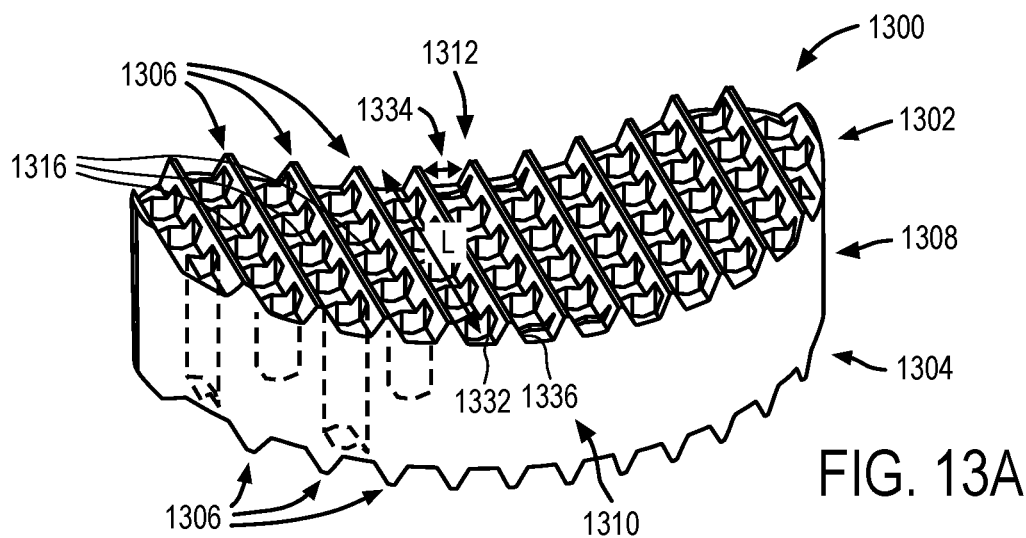
FIG. 13A shows a perspective view of an aspect of a processing operation for forming an interbody spinal implant having surface features and graft features.
Figure 13B:
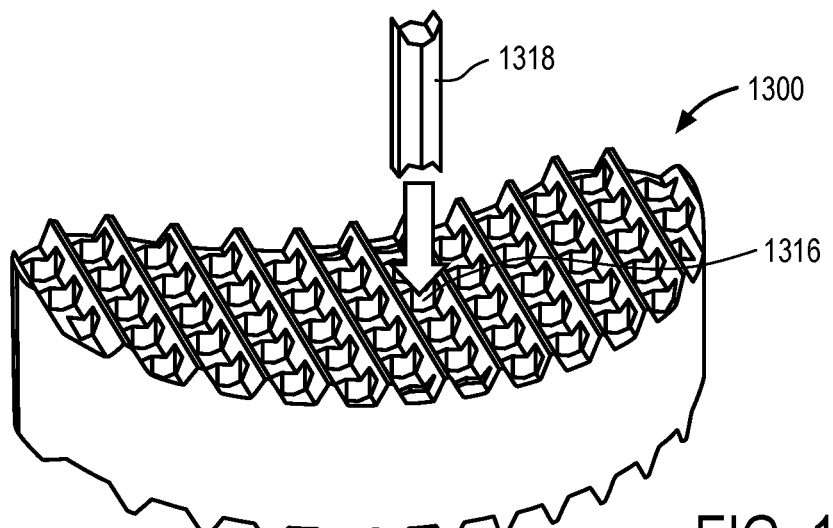
FIG. 13B shows a perspective view of an aspect of a further processing operation for forming the interbody spinal implant having surface features and graft features of FIG. 13A.
Figure 13C:
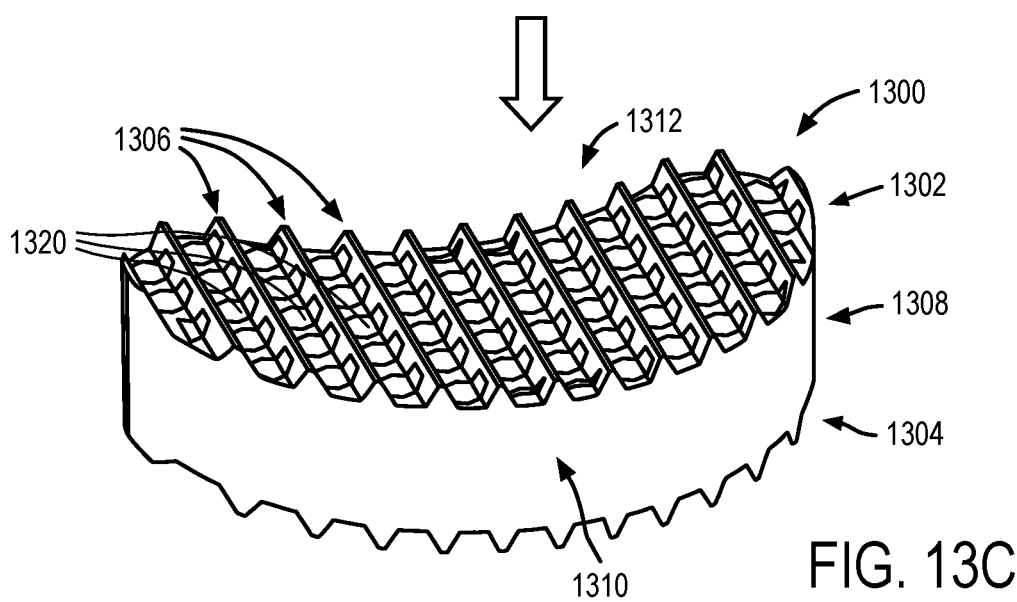
FIG. 13C shows a perspective view of an aspect of a further processing operation for forming the interbody spinal implant having surface features and graft features of FIG. 13A-B.

Further implant configurations including both raised surface features and/or embedded graft features will now be described in more detail in reference to FIGS. 13A-17B. FIGS. 13A-13C are perspective side views of one aspect of an implant, and process for manufacturing an implant, having raised surface features and embedded graft features. Implant 1300 may be substantially similar to the previously discussed implants in that it may be a unibody cage including a first (top) side 1302, a second (bottom) side 1304, lateral sides 1308, an anterior side 1310 and a posterior side 1312. In some aspects, the lateral side 1308, anterior side 1310 and/or posterior side 1312 alone, or in combination, may also be referred to herein as a connector, a body, a column, or any other structure suitable for connecting first (top) side 1302 to second (bottom) side 1304. In some aspects, the first (top) side 1302 may be considered or referred to herein as a superior side (having a superior surface) of the implant and the second (bottom) side 1304 may be considered or referred to herein as an inferior side (having an inferior surface) of the implant. The superior and/or inferior surfaces of the first (top) side 1302 and second (bottom) side 1304 that contact the anatomical structures of the patient may therefore be considered bone contacting surfaces and include raised surface features 1306 that increase a bone contacting surface area and/or enhance bone growth on or in the implant 1300. In addition to raised surface features, implant 1300 may include embedded graft features 1320 as illustrated by FIG. 13C.

In some aspects, raised surface features 1306 may be similar to the previously discussed surface features in that they have a uniform size and shape, and are arranged in a pattern, or so that they repeat in a uniform and continuous manner. Representatively, in one aspect, surface features 1306 may be considered to be arranged in a linear pattern. In the illustrated configuration, surface features 1306 are elongated continuous structures having a length dimension (L) that extends from anterior side 1310 to posterior side 1312 of implant 1300. Surface features 1306 may be arranged in a pattern in which their length dimensions (L) run parallel to one another. Surface features 1306 may have peaks that are pointed, flat or curved. In some aspects, surface features 1306 may have a substantially triangular cross-sectional shape. In still further aspects, a height of each of surface features 1306 may be the same, or substantially the same, such that they are considered coplanar with one another. In addition, each of surface features 1306 may be separated from adjacent surface features 1306 by a trough, recess, groove or channel 1332 defining a gap 1334 in between each peak 1330. The channel 1332 may be defined by the side walls 1336 of adjacent surface features 1306. As a result of the shape of the surface features 1306, the surface area of implant 1300 is increased when compared to a flat surface resulting in a greater surface area for bone growth in or on the implant 1300. It should further be understood that although surface features 1306 are shown on only the superior and inferior sides 1302, 1304 of implant 1300, they could be formed on any side of the implant to enhance bone growth on or in the implant 1300. In addition, although surface features 1306 are shown on a unibody implant, it should be understood that surface features 1306 may be applied to any interbody device (e.g., an expandable cage) or device in general having a bone contacting surface in which enhanced bone growth on or in the implant is desired.

Referring now to embedded graft features 1320, as can be seen from FIG. 13C, graft features 1320 are embedded within implant 1300 in or between each of the surface features 1306. The term "embedded" is intended to mean that the graft features 1320 are fixed within, and surrounded by, the material used to form the implant 1300. Representatively, graft features 1320 may be arranged in a linear pattern within channels 1332 between each of the surface features 1320. In some aspects, graft features 1320 may be embedded in the channels 1332 as well as portions of the surface feature side walls 1336 forming the channels 1332. The graft features 1320 may be made of any type of graft material that promotes or otherwise enhances bone growth on or in the implant 1300. For example, the graft features 1320 may be made of an allograft bone material or a non-allograft bone material.

The graft features 1320 may be embedded or otherwise formed within the implant 1300 during manufacturing of the implant such that they are already formed in the implant prior to use by the surgeon. Representatively, in one aspect, an implant 1300 having surface features 1306 is provided, and then holes 1316 are formed within the first (top) side 1302 and/or second (bottom) side 1304 as shown in FIG. 13A. Holes 1316 may be formed in the desired locations for the graft features 1320, for example, between or in the surface features 1306. Holes 1316 may have a size and shape of the desired graft features 1320. Holes 1316 may extend partially through implant 1300 as shown in FIG. 13A such that the graft features are formed partially through the implant 1300. In other aspects, holes 1316 may extend entirely through implant from first (top) side 1302 to second (bottom) side 1304 such that the graft features extend entirely through the implant 1300. In some aspects, implant 1300 may include one or more of holes 1316 formed partially and/or entirely through implant 1300 as shown. As shown in FIG. 13B, discrete pieces or plugs of graft material 1318 that are in a size and shape corresponding to holes 1316 may then be inserted into each of holes 1316 as illustrated by the arrow. In one aspect, the pieces or plugs of graft material 1318 may be pressed in, glued in, have retaining features, swaged in, or some other processing operation may be used to insert the pieces of graft material 1318 within holes 1316. Once each of the discrete plugs of graft material 1318 are inserted or embedded into holes 1316, an implant 1300 having embedded graft features 1320 and raised surface features 1306 is formed as shown in FIG. 13C. It should further be understood that in addition to improving or enhancing bone growth on or in the implant 1300, embedding of the graft features 1320 within implant 1300 may also help reduce possible subsidence of the implant and/or help with load bearing. Representatively, the formation of the holes 1316 within implant 1300 may help reduce large spans of unsupported implant portions, which may be found in other interbody implants without holes 1316, and the graft materials 1318 therein may increase the surface area for bearing vertebral body loads.

Figure 14A:
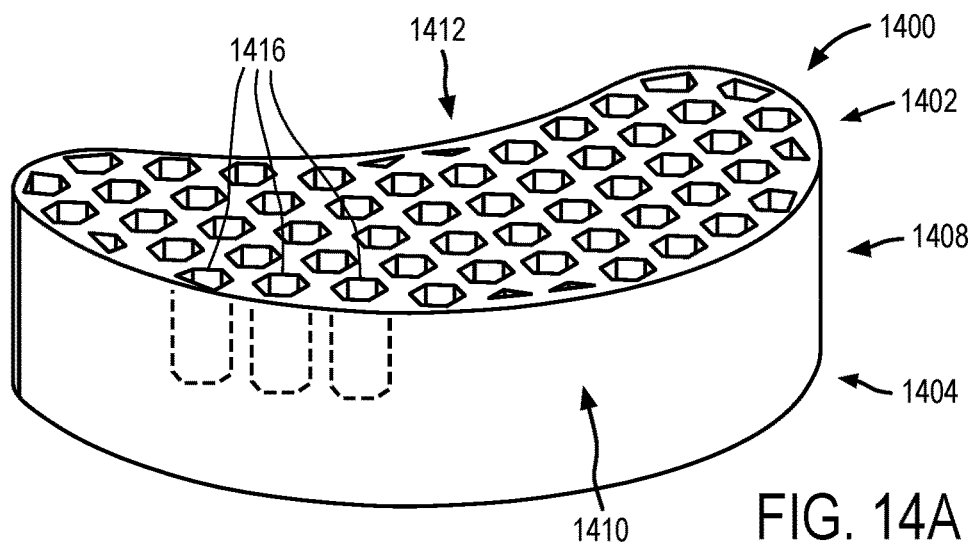
FIG. 14A shows a perspective view of an aspect of a processing operation for forming an interbody spinal implant having surface features and graft features.
Figure 14B:
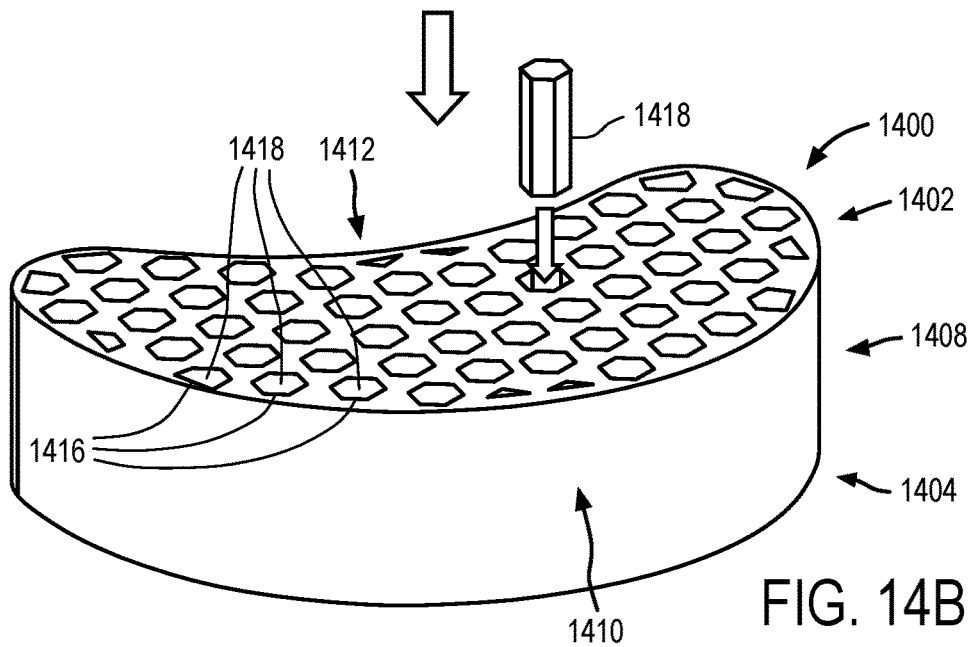
FIG. 14B shows a perspective view of an aspect of a further processing operation for forming the interbody spinal implant having surface features and graft features of FIG. 14A.
Figure 14C:
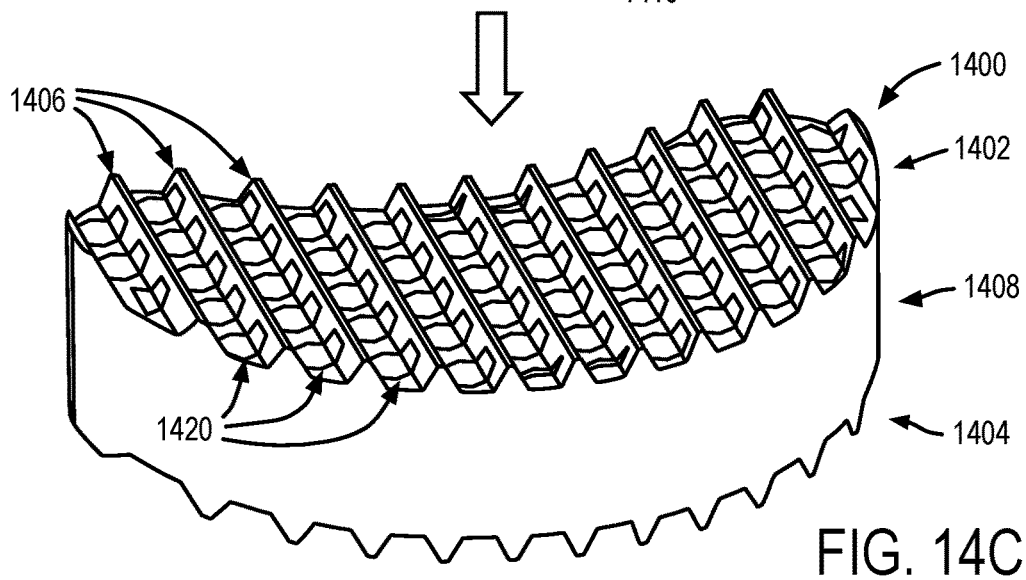
FIG. 14C shows a perspective view of an aspect of a further processing operation for forming the interbody spinal implant having surface features and graft features of FIG. 14A-B.

FIG. 14A-14C illustrates another series of processing operations for manufacturing an implant having surface features and embedded graft features. Implant 1400 may be substantially similar to the previously discussed implants in that it may be a unibody cage including a first (top) side 1402, a second (bottom) side 1404, lateral sides 1408, an anterior side 1410 and a posterior side 1412. In some aspects, the lateral side 1408, anterior side 1410 and/or posterior side 1412 alone, or in combination, may also be referred to herein as a connector, a body, a column, or any other structure suitable for connecting first (top) side 1402 to second (bottom) side 1404. In some aspects, the first (top) side 1402 may be considered or referred to herein as a superior side (having a superior surface) of the implant and the second (bottom) side 1404 may be considered or referred to herein as an inferior side (having an inferior surface) of the implant. The superior and/or inferior surfaces of the first (top) side 1402 and second (bottom) side 1404 that contact the anatomical structures of the patient may therefore be considered bone contacting surfaces and include raised surface features 1406 and graft features 1420 that increase a bone contacting surface area and/or enhance bone growth on or in the implant 1400 as previously discussed in reference to FIGS. 13A-C. The graft features 1420 may be embedded or otherwise formed within the implant 1400 during manufacturing of the implant such that they are already formed in the implant prior to use by the surgeon as previously discussed. In this aspect, however, an implant 1400 without surface features formed therein is provided, and then holes 1416 are formed within the first (top) side 1402 and/or second (bottom) side 1404 in a linear pattern as shown in FIG. 14A. Holes 1416 may be formed in the desired locations for the graft features 1420, for example, so that they are between or in surface features that will be formed later. Holes 1416 may have a size and shape of the desired graft features 1420. As shown in FIG. 14B, discrete pieces or plugs of graft material 1418 that are in a size and shape corresponding to holes 1416 may then be inserted or packed into each of holes 1416 as illustrated by the arrow. Once each of the discrete plugs of graft material 1418 are inserted into holes 1416, the implant 1400 with embedded graft features 1420 may be machined to form the surface features 1406 as previously discussed. An implant 1400 having embedded graft features 1420 and raised surface features 1406 is formed as shown in FIG. 14C.

Figure 15A:
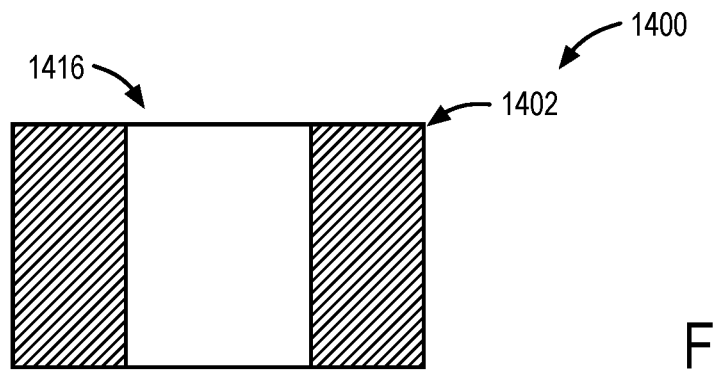
FIG. 15A shows a magnified perspective view of an aspect of a processing operation for forming graft features in an interbody spinal implant.
Figure 15B:
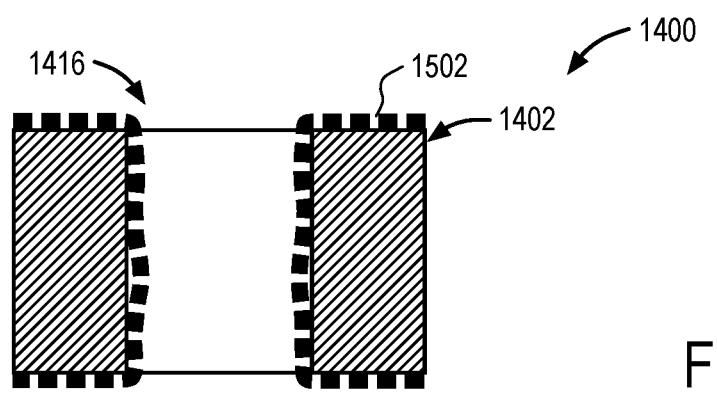
FIG. 15B shows a magnified perspective view of an aspect of a further processing operation for forming graft features in the interbody spinal implant of FIG. 15A.

It is further contemplated that in another aspect, instead of using discrete plugs or pieces of preformed graft material 1318, 1418, the graft material may be applied in layers that fill the holes formed in the implant 1300, 1400. Representatively, FIG. 15A-15D illustrates another series of processing operations for manufacturing an implant by applying layers of graft material to form embedded graft features. In particular, FIGS. 15A-D show magnified cross-sectional views of one of holes 1416 formed in the first (top) side 1402 of implant 1400 previously discussed in reference to FIG. 14A. As can be seen from FIG. 15A, hole 1416 includes an opening through the first (top) side 1402 of implant 1400. The implant 1400 may then be dipped into a graft material solution that deposits a layer 1502 of graft material to the walls of the hole 1416 as shown in FIG. 15B. In another aspect, the layer 1502 of graft material could be applied by a spraying technique (e.g., HA coating), deposited using static electricity to deposit particles then baked on, or an additive/3D printing technique. For example, an additive technique may include successive layering of the graft material onto the implant. Each layer may be allowed to partially or fully solidify before the next layer is laid.

Figure 15C:
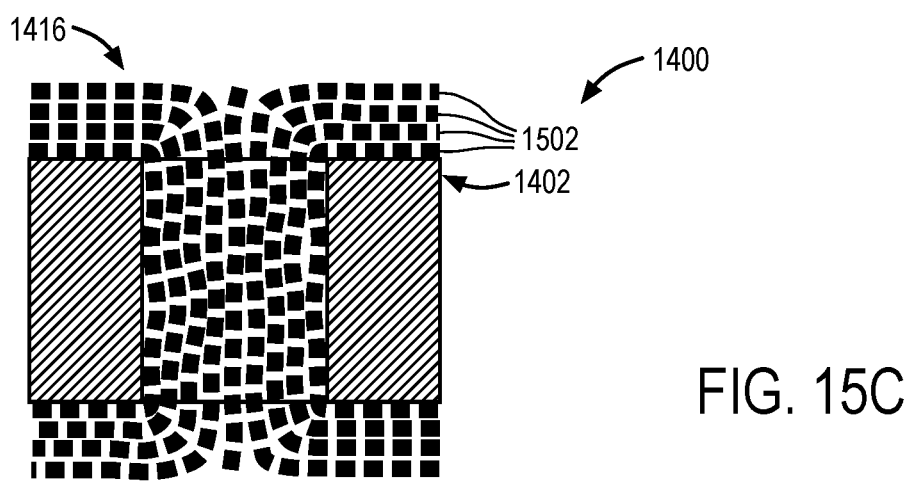
FIG. 15C shows a magnified perspective view of an aspect of a further processing operation for forming graft features in the interbody spinal implant of FIG. 15A-B.
Figure 15D:
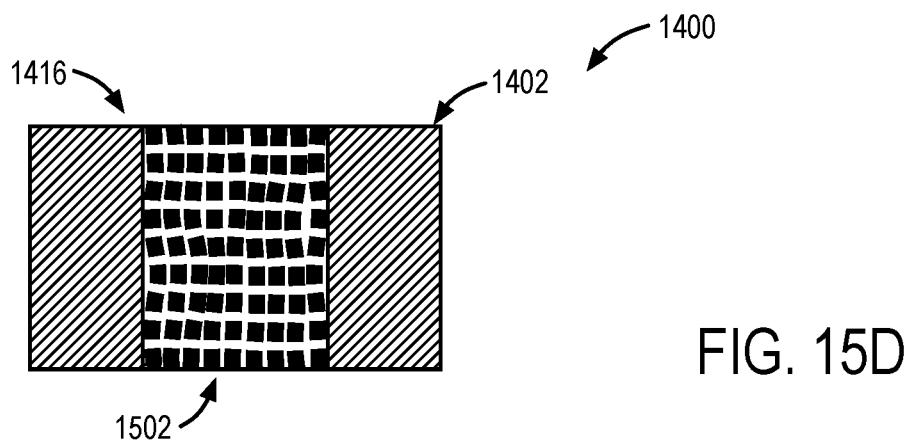
FIG. 15D shows a magnified perspective view of an aspect of a further processing operation for forming graft features in the interbody spinal implant of FIG. 15A-C.

Each layer 1502 may have a substantially uniform thickness, or could have different thickness throughout. This processing operation of applying layer 1502 may be repeated until the hole 1416 is completely filled with the graft material as shown in FIG. 15C. Implant 1400 may then be machined to remove any graft material layer 1502 remaining on the top surface of the first (top) side 1402 so that the graft material layer 1502 is completely embedded within hole 1416 and flush with the side 1402 as shown in FIG. 15D. In addition, in some aspects, after machining, the implant 1400 may be subjected to surface treatments to, for example, form surface features or other surface structures within implant 1400 to improve and/or enhance bone growth on or in the implant 1400. In addition, in some aspects, it may be desirable to leave one or more of the holes 1416 partially open/through to allow some easy flow from the superior to inferior surfaces (e.g., leave a hole down the middle that is not fully filled with the graft material).

Figure 16A:
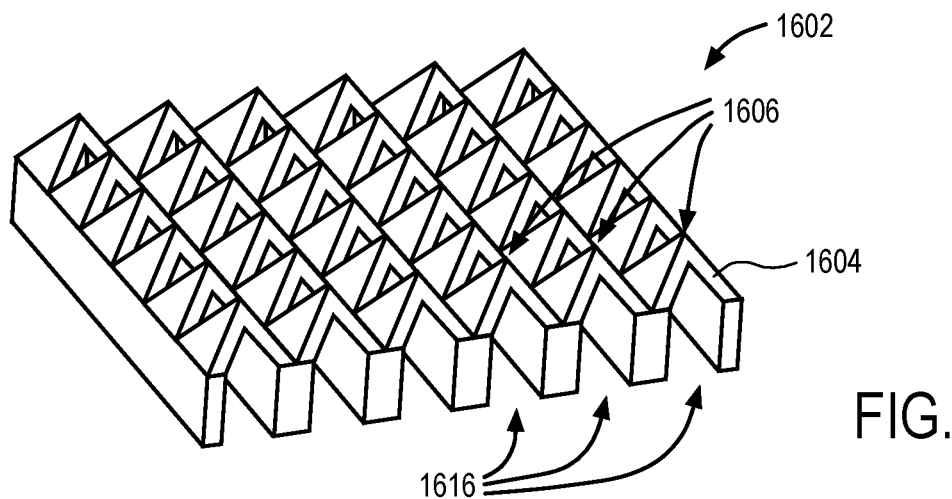
FIG. 16A shows a perspective view of an aspect of a processing operation for forming an interbody spinal implant having surface features and graft features.
Figure 16B:
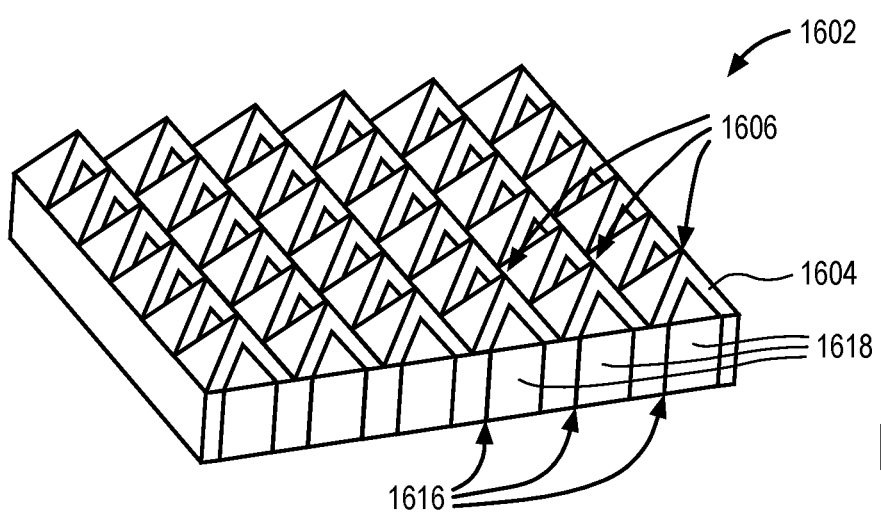
FIG. 16B shows a perspective view of an aspect of a further processing operation for forming the interbody spinal implant having surface features and graft features of FIG. 16A.
Figure 16C:
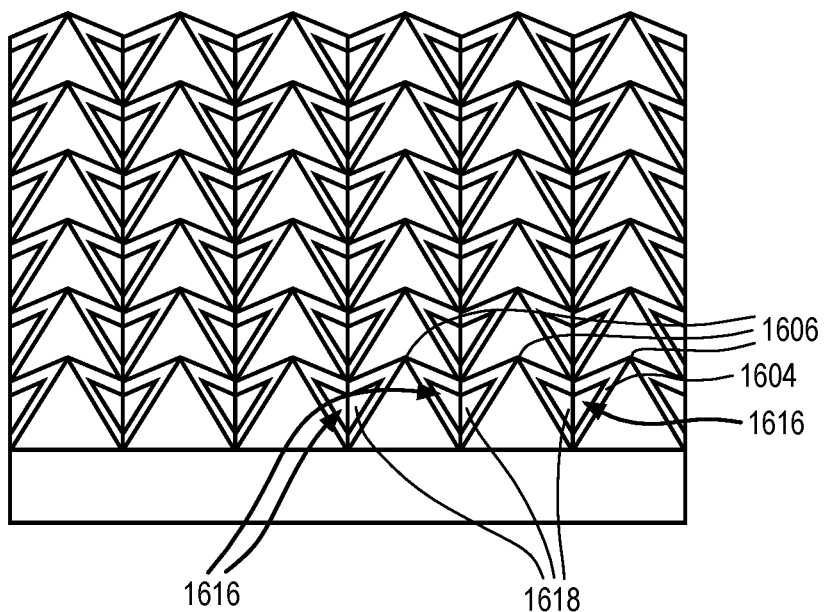
FIG. 16C shows a perspective view of an aspect of a further processing operation for forming the interbody spinal implant having surface features and graft features of FIG. 16A-B.
Figure 17A:
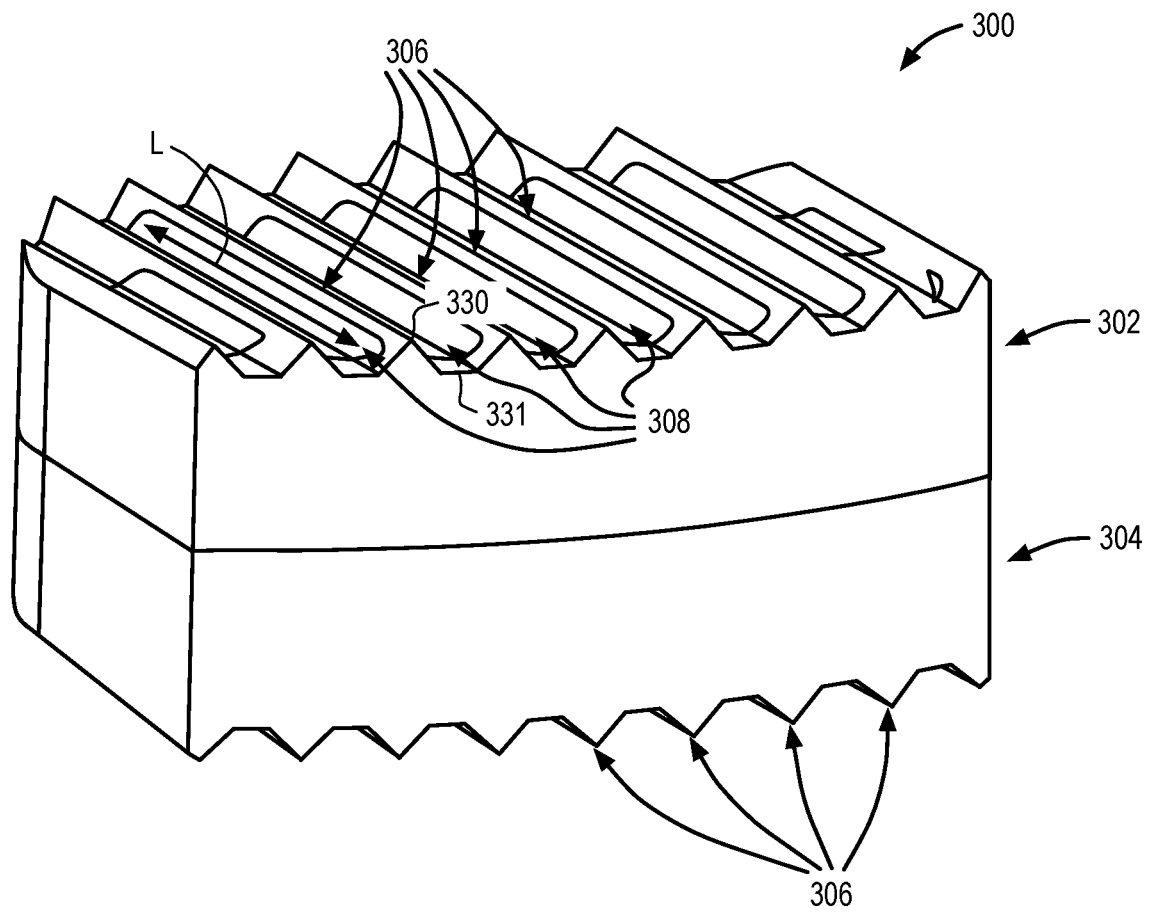
FIG. 17A shows a perspective view of one aspect of an interbody spinal implant in a collapsed configuration.
Figure 17B:
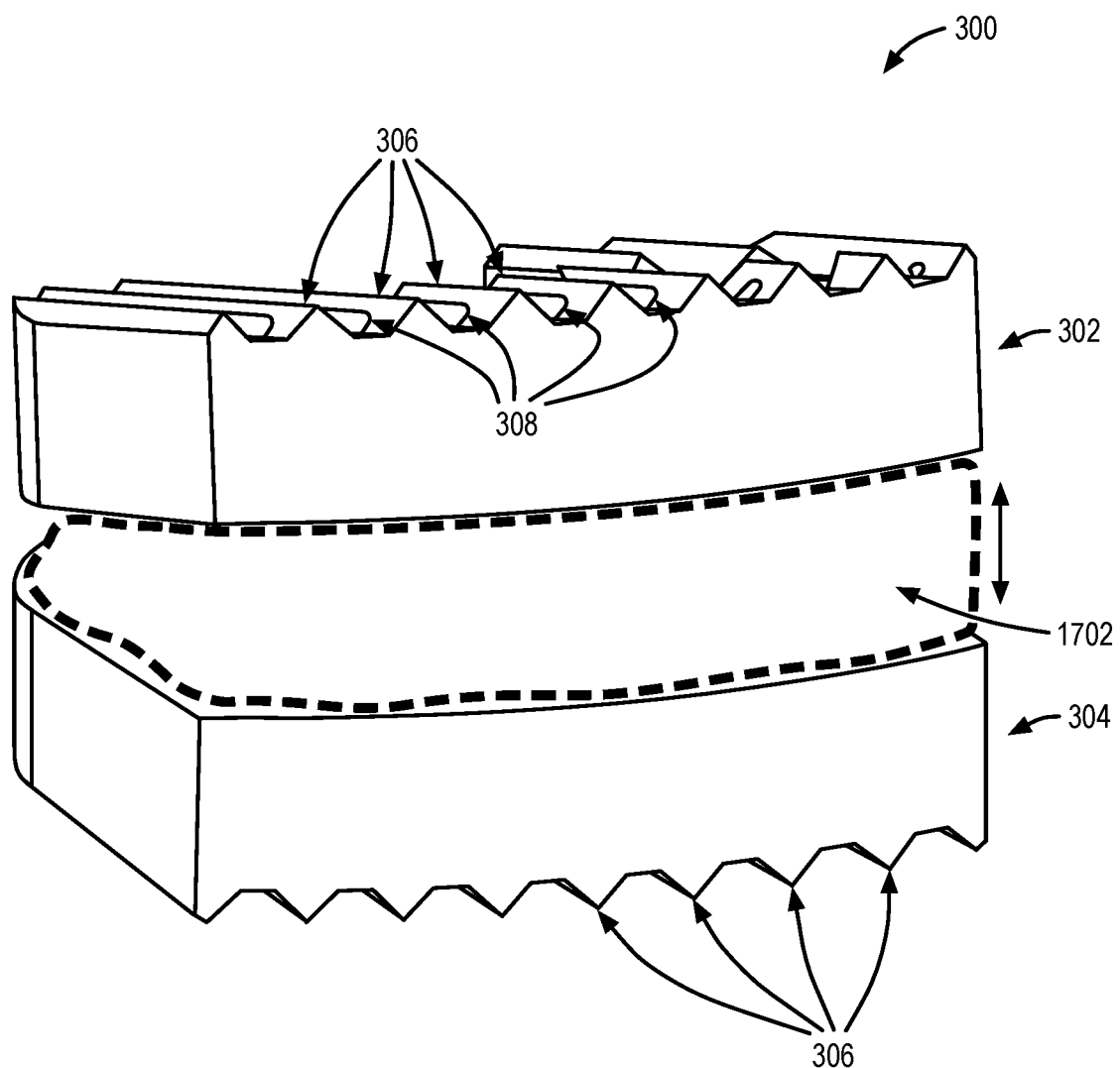
FIG. 17B shows a perspective view of one aspect of an interbody spinal implant in an expanded configuration.

Referring now to FIG. 16A-16C, FIGS. 16A-C illustrate another series of processing operations for manufacturing an implant having surface features and embedded graft features. Representatively, FIGS. 16A-C illustrate a magnified perspective view of a first (top) side 1602 of an implant (e.g., any one or more of the previously discussed implants) having surface features 1606 formed therein. In this aspect, the surface features 1606 may be pyramid shaped structures that are formed in or on the bone contacting surface of the first (top) side 1602. Each of surface features 1606 may have a front face 1604 within which the embedded graft features 1618 are formed as shown in FIGS. 16B-C. Representatively, an opening 1616 may be formed within the front face 1604 of each of the surface features 1606. A graft material is then inserted or embedded within the opening 1616 as previously discussed to form the embedded graft features 1606 within the surface features 1606 as shown in FIG. 16B-C. The graft features 1618 may be embedded or otherwise formed within the first (top) side 1602 of the implant during manufacturing of the implant such that they are already formed in the implant prior to use by the surgeon as previously discussed. In addition, it should be understood that although surface features 1606 and graft features 1618 are shown in side 1602, surface features 1606 and graft features 1618 may be formed in any side or surface of any one or more of the previously discussed implants. In some aspects, the graft material may be substantially softer than the interbody cage material such that it is shielded during insertion and residence in the interbody space. This could allow easy integration of bone with the graft due to its relative softness, yet not have VB loading destroy or damage it during loading or usage Referring now to FIG. 17A-17B, FIG. 17A-B illustrate perspective view of one aspect of an expandable interbody device. Representatively, in one aspect, implant 300 shown in FIGS. 17A-B may be an expandable or adjustable corpectomy cage as previously discussed in reference to FIG. 3. FIG. 17A shows implant 300 in a collapsed state and FIG. 17B shows implant 300 in an expanded state. As previously discussed, implant 300 may include a first (top) endplate 302 connected to a second (bottom) endplate 304 by a connector 310. In some aspects, the connector 310 may be considered a body, a column, a lateral side, or any other structure suitable for connecting first endplate 302 to second endplate 304. The first (top) endplate 302 and the second (bottom) endplate 304 may move towards or away from each other in the direction of the arrow (see FIG. 17B) to expand, contract, or otherwise adjust the implant. As can further be seen from FIGS. 17A-B, the bone contacting surfaces of the first (top) endplate 302 and second (bottom) endplate 306 may include, or be considered formed by, raised surface features 306 and/or embedded graft features 308 that promote or otherwise enhance bone growth on or in the implant 300. The raised surface features 306 may be similar to any of the previously discussed surface features in that they may be arranged in a pattern (e.g., a linear pattern) and run parallel to one another. The surface features 306 may have peaks 330 and include substantially triangular cross-sectional shapes as previously discussed. Surface features 306 may further be separated from one another by troughs or channels 332 which are formed by the side walls of the surface features 306 as previously discussed.

Graft features 308 may be embedded or inserted within the troughs 332 and/or side walls of surface features 306 as shown in FIGS. 17A-B according to any of the previously discussed processing operations during manufacture. For example, graft features 308 may be pre-formed pieces or plugs of graft material that are inserted within openings or recesses between surface features 306 in a desired arrangement or pattern. Representatively, graft features 308 may be elongated structures having a length dimension (L) that is arranged parallel to the length dimension of the surface features 306. For example, the graft features 308 may run parallel to the surface features 306. The graft features 308 may be of a size and shape suitable to cover a desired surface area of the implant to improve or enhance bone growth on or in implant 300.

It should be recognized that one advantage of the illustrated configuration is that with the graft features 308 integrally formed in or on the first (top) endplate 302 and second (bottom) endplate 304 during manufacture, less graft within the device is needed. In addition, the graft features 308 may provide more surface area contact of the graft material even when in the collapsed configuration of FIG. 17A. Moreover, in the expanded configuration of FIG. 17B, it is contemplated that more graft material 1702 could be added between the first (top) endplate 302 and second (bottom) endplate 304 by the surgeon as shown in FIG. 17B. The graft material 1702 may be a porous graft material that could allow bone to grow through the implant endplates so that the graft is increasing accessibility to the bone.

While certain aspects have been described and shown in the accompanying drawings, it is to be understood that such aspects are merely illustrative of and not restrictive on the broad invention, and that the disclosure is not limited to the specific constructions and arrangements shown and described, since various other modifications may occur to those of ordinary skill in the art. For example, although in some aspects the endplates (e.g., superior and inferior surfaces 402, 404) are shown as flat, they may be curved, uniconvex or bioconvex. In addition, one or more of the endplates may be at an angle to each other, such as lordotic (e.g., an angle opening to the front of the implant body) and/or kyphotic (e.g., an angle opening to the posterior of the implant body) to correct sagittal balance, or at an angle opening to the side to correct coronal imbalance. The description is thus to be regarded as illustrative instead of limiting. In addition, to aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What is claimed is:

1. An interbody spinal implant comprising:
a body portion comprising a superior side, an inferior side and a lateral side connecting the superior side and the inferior side, at least one of the superior side or the inferior side comprises a bone contacting surface operable to be coupled to an anatomical structure of a patient;
a plurality of uniform features formed in the bone contacting surface, wherein each uniform feature of the plurality of uniform features comprises a planar peak or a rounded peak each separated by one or more graft feature troughs, wherein each uniform feature comprises a continuous length dimension extending from an anterior side to a posterior side of the body portion, wherein the plurality of uniform features are uniformly distributed across the least one of the superior side or the inferior side, and wherein a width of the plurality of uniform features decreases from a first width to a second width along a direction towards a center of the body portion; and
a material layer comprising surface structures coupled to the plurality of uniform features to increase a surface area of the bone contacting surface to promote bone growth, wherein the material layer is substantially planar such that one or more recesses are present between a plane of the material layer and the one or more graft feature troughs, and wherein the material layer is substantially parallel to the continuous length dimension.

2. The interbody spinal implant of claim 1 wherein the plurality of uniform features is arranged in a linear pattern and each of the uniform features are discrete protrusions arranged to form the linear pattern.

3. The interbody spinal implant of claim 1 wherein each uniform feature comprises an undercut, and wherein the undercut of adjacent features forms a trough between each of the uniform features.

4. The interbody spinal implant of claim 1 wherein the material layer comprises a mesh welded to the planar peak or the round peak of the plurality of uniform features.

5. The interbody spinal implant of claim 1 further comprising a surface coating coupled to the plurality of uniform features.

6. The interbody spinal implant of claim 1 wherein the body portion is a unibody cage.

7. The interbody spinal implant of claim 1 wherein the plurality of uniform features extend along a first direction from the superior side or extend along a second direction from the inferior side, and wherein the material layer is substantially perpendicular to the first direction, the second direction, or both.

8. The interbody spinal implant of claim 1 wherein the plurality of uniform features comprise the planar peaks, and wherein the plurality of uniform features comprise a substantially triangular cross-sectional shape.

9. An interbody spinal implant comprising:
a cage having a superior side connected to an inferior side, at least one of the superior side or the inferior side comprises a bone contacting surface operable to be coupled to an anatomical structure of a patient;

a plurality of raised features formed in the bone contacting surface, wherein the plurality of raised features is dimensioned to increase a surface area of the bone contacting surface, and wherein a width of the plurality of raised features decreases from a first width to a second width along a direction towards a center of the cage, wherein the plurality of raised features comprises a continuous length dimension extending from an anterior side to a posterior side of the body portion, and wherein the plurality of raised features is uniformly distributed across the least one of the superior side or the inferior side;

a plurality of graft features embedded in the bone contacting surface, wherein the plurality of graft features comprise at least one graft feature positioned between each raised feature of the plurality of raised features that promotes bone growth through the bone contacting surface; and a material layer comprising surface structures coupled to the plurality of raised features to further increase the surface area of the bone contacting surface, wherein the material layer is substantially planar such that one or more recesses are present between a plane of the material layer and the plurality of graft features, and wherein the material layer is substantially parallel to the continuous length dimension.

10. The interbody spinal implant of claim 9 wherein the plurality of raised features and the plurality of graft features are arranged in an alternating linear pattern.

11. The interbody spinal implant of claim 9 wherein the at least one graft feature comprises a length dimension that runs parallel to a length dimension of the plurality of raised features.

12. The interbody spinal implant of claim 9 wherein the plurality of graft features is embedded in the plurality of raised features.

13. The interbody spinal implant of claim 9 wherein the cage comprises a first endplate forming the superior side and a second endplate forming the inferior side.

14. The interbody spinal implant of claim 9 wherein the material layer is substantially perpendicular to an anterior side, a posterior side, or both of the cage.

* * * * *